US006939855B2

(12) United States Patent
Yednock et al.

(10) Patent No.: US 6,939,855 B2
(45) Date of Patent: Sep. 6, 2005

(54) ANTI-INFLAMMATORY COMPOSITIONS AND METHOD

(75) Inventors: Theodore A. Yednock, Forest Knolls, CA (US); Michael A. Pleiss, Sunnyvale, CA (US)

(73) Assignees: Elan Pharmaceuticals, Inc., South San Francisco, CA (US); Wyeth, Philadelphia, PA (US)

( * ) Notice: Subject to any disclaimer, the term of this patent is extended or adjusted under 35 U.S.C. 154(b) by 5 days.

(21) Appl. No.: 09/127,364

(22) Filed: Jul. 31, 1998

(65) Prior Publication Data

US 2002/0039745 A1 Apr. 4, 2002

Related U.S. Application Data

(60) Provisional application No. 60/112,020, filed on Jul. 31, 1997, now abandoned, and provisional application No. 60/054,453, filed on Aug. 1, 1997.

(51) Int. Cl.[7] .................................................. C07K 5/06
(52) U.S. Cl. .......................... 514/19; 548/535; 562/445
(58) Field of Search ................................ 514/19, 2, 18; 548/535; 562/445; 530/331; 435/7.1

(56) References Cited

U.S. PATENT DOCUMENTS

| | | | |
|---|---|---|---|
| 4,018,913 A | 4/1977 | Okamoto et al. | 514/20 |
| 4,018,915 A | 4/1977 | Okamoto et al. | 514/20 |
| 4,036,955 A | 7/1977 | Okamoto et al. | 514/20 |
| 4,041,156 A | 8/1977 | Okamoto et al. | 514/20 |
| 4,046,876 A | 9/1977 | Okamoto et al. | 514/20 |
| 4,055,636 A | 10/1977 | Okamoto et al. | 514/20 |
| 4,055,651 A | 10/1977 | Okamoto et al. | 514/319 |
| 4,069,318 A | 1/1978 | Okamoto et al. | 514/20 |
| 4,070,457 A | 1/1978 | Okamoto et al. | 514/510 |
| 4,071,621 A | 1/1978 | Okamoto et al. | 514/20 |
| 4,073,914 A | 2/1978 | Kikumoto et al. | 514/319 |
| 4,096,255 A | 6/1978 | Kikumoto et al. | 514/227.5 |
| 4,097,591 A | 6/1978 | Okamoto et al. | 514/20 |
| 4,104,392 A | 8/1978 | Okamoto et al. | 514/307 |
| 4,260,601 A | 4/1981 | Reichelt | 514/18 |
| 4,804,676 A | 2/1989 | Inaoka et al. | 514/423 |
| 4,910,190 A | 3/1990 | Bergeson et al. | 514/19 |
| 4,977,168 A | 12/1990 | Bernat et al. | 514/19 |
| 4,981,873 A | 1/1991 | Witte et al. | 514/562 |
| 4,992,421 A | 2/1991 | De | 514/19 |
| 5,338,755 A | 8/1994 | Wagnon et al. | 514/414 |
| 5,362,902 A | 11/1994 | Barnish et al. | 560/13 |
| 5,397,801 A | 3/1995 | Wagnon et al. | 514/418 |
| 5,481,005 A | 1/1996 | Wagnon et al. | 548/537 |
| 5,578,633 A | 11/1996 | Wagnon et al. | 514/418 |
| 5,650,428 A | 7/1997 | Ohmori et al. | 514/419 |
| 5,688,913 A | 11/1997 | Arrhenius et al. | 530/330 |
| 6,001,809 A | 12/1999 | Thorsett et al. | 514/15 |
| 6,093,696 A | 7/2000 | Head et al. | 514/19 |
| 6,110,945 A | 8/2000 | Head et al. | 514/332 |
| 6,197,794 B1 | 3/2001 | Head et al. | 514/342 |
| 6,221,888 B1 | 4/2001 | Durette et al. | 514/357 |
| 6,229,011 B1 | 5/2001 | Chen et al. | 544/171 |
| 6,239,108 B1 | 5/2001 | Lin et al. | 514/15 |
| 6,248,713 B1 | 6/2001 | Lin et al. | 514/2 |
| 6,265,572 B1 | 7/2001 | Chen et al. | 540/453 |
| 6,274,577 B1 | 8/2001 | Brown et al. | 710/110 |
| 6,288,267 B1 | 9/2001 | Hull et al. | 560/149 |
| 6,306,840 B1 | 10/2001 | Adams et al. | 514/109 |
| 6,329,362 B1 | 12/2001 | Achribald et al. | 514/188 |
| 6,329,372 B1 | 12/2001 | Head et al. | 514/241 |

FOREIGN PATENT DOCUMENTS

| | | |
|---|---|---|
| AU | 6147073 | 4/1975 |
| DE | 23 57 334 | 6/1974 |
| DE | 26 55 636 | 6/1977 |
| EP | 0 526 348 | 2/1993 |
| GB | 9711143.9 | 5/1997 |
| GB | 9714314.3 | 7/1997 |
| GB | 9714316.8 | 7/1997 |
| GB | 9714335.8 | 7/1997 |
| GB | 9722674.0 | 10/1997 |
| GB | 9800680.2 | 1/1998 |
| GB | 9800684.4 | 1/1998 |
| GB | 9800686.9 | 1/1998 |
| JP | 04 154732 | 5/1992 |
| JP | 06 016625 | 1/1994 |
| JP | 08 073422 | 3/1996 |
| WO | 92/16549 | 10/1992 |
| WO | 94/07815 | 4/1994 |
| WO | 94/12181 | 6/1994 |
| WO | 95/15973 | 6/1995 |
| WO | 96/01644 | 1/1996 |
| WO | 96/20725 | 7/1996 |
| WO | 96/20949 | 7/1996 |
| WO | 96/22966 | 8/1996 |
| WO | 97/03094 | 1/1997 |
| WO | 97/48726 | 12/1997 |
| WO | 98/04247 | 2/1998 |
| WO | 98/42656 | 10/1998 |
| WO | 98/53814 | 12/1998 |
| WO | 98/53817 | 12/1998 |
| WO | 98/53818 | 12/1998 |
| WO | 98/54207 | 12/1998 |
| WO | 98/58902 | 12/1998 |
| WO | 99/06432 | 2/1999 |
| WO | 99/06436 | 2/1999 |
| WO | 99/10312 | 3/1999 |
| WO | 99/10313 | 3/1999 |
| WO | 99/67230 | 12/1999 |

OTHER PUBLICATIONS

Theien, B. E. (Journal of Clinical Investigation 107 (8) 995–1006, 2001).*
Smith (J Biol Chem 271, 28485, 1996).*
Palmer (J Cell Biol 123, 1289, 1993).*

(Continued)

*Primary Examiner*—Jon Weber
*Assistant Examiner*—David Lukton
(74) *Attorney, Agent, or Firm*—Foley & Lardner LLP

(57) ABSTRACT

The disclosed invention includes pharmaceutical compositions and methods for treating inflammatory conditions, particularly those that are characterized by increased binding of alpha-9 integrin to one or more of its ligands. Also disclosed are methods for selecting compounds for use in such compositions and methods.

8 Claims, 1 Drawing Sheet

U.S. PATENT DOCUMENTS

| | | | |
|---|---|---|---|
| 6,348,463 B1 | 2/2002 | Head et al. | 514/241 |
| 6,362,204 B1 | 3/2002 | Head et al. | 514/342 |
| 6,369,229 B1 | 4/2002 | Head et al. | 546/264 |
| 6,376,538 B1 | 4/2002 | Adams et al. | 514/466 |
| 6,380,387 B1 | 4/2002 | Sidduri et al. | 544/311 |
| 6,388,084 B1 | 5/2002 | Kaplan et al. | 546/291 |
| 6,403,608 B1 | 6/2002 | Langham et al. | 514/309 |
| 6,407,066 B1 | 6/2002 | Dressen et al. | 514/19 |
| 6,420,600 B1 | 7/2002 | Sidduri et al. | 562/575 |
| 6,423,688 B1 | 7/2002 | Thorsett et al. | 514/19 |
| 6,423,728 B1 | 7/2002 | Hull et al. | 514/357 |
| 6,426,348 B1 | 7/2002 | Hull et al. | 514/256 |
| 6,436,904 B1 | 8/2002 | Ashwell et al. | 514/19 |
| 6,455,539 B2 | 9/2002 | Langham et al. | 514/300 |
| 6,455,550 B1 | 9/2002 | Chen et al. | 514/341 |
| 6,458,844 B2 | 10/2002 | Hull et al. | 514/599 |

OTHER PUBLICATIONS

Yokosaki, Yasuyuki (J. Biol Chem 269(43), 26691–96, 1994).*

U.S. Appl. No. 60/086,241 USA filed Mar. 21, 1997.*
U.S. Appl. No. 60/022,890 USA filed Jul. 25, 1996.*
U.S. Appl. No. 60/032,786 USA filed Dec. 6, 1996.*
U.S. Appl. No. 60/047,856 USA filed May 29, 1997.*
U.S. Appl. No. 60/047,954 USA filed May 29, 1997.
U.S. Appl. No. 60/048,017 USA filed May 29, 1997.
U.S. Appl. No. 60/066,525 USA filed Nov. 25, 1997.
U.S. Appl. No. 60/066,787 USA filed Nov. 25, 1997.
U.S. Appl. No. 60/066,831 USA filed Nov. 25, 1997.*
U.S. Appl. No. 08/821,825 USA filed Mar. 21, 1997.*

Archibald, S.C., et al., "Discovery and Evaluation of Potent, Tyrosine–Based α4β1 Integrin Antagonists", *Bioorg & Med. Chem. Lett.*, vol. 10, pp. 997–999 (2000).

Crossley, M.J., et al. "Studies on the Effects of Pharmacological Agents on Antigen–Induced Arthritis in BALB/c Mice." *Drugs Exptl. Clin. Res.* XIII(5): 273–277 (1987).

Dutta, A.S., et al. "Potent Cyclic Monomeric and Dimeric Peptide Inhibitors of VLA–4 (α4β1 Integrin)–Mediated Cell Adhesion Based on the Ile–Leu–Asp–Val Tetrapeptide." *J. Peptide Sci.* 6: 321–341 (2000).

El–Naggar, A.M., et al., *Acta. Pharm. Jugosl.* (1985), 35(1), 15–22.

Engleman, V.W., et al. "Cell Adhesion Integrins as Pharmaceutical Targets." *Ann. Reports in Med. Chem.* 31: 191–200 (1996).

Ewenson, A. et al., "Analogues of Substance P Containing an α–hydroxy, β–amino acid: Synthesis and Biological Activity", *Eur. J. Med. Chem.*, vol. 26, pp. 435–442 (1991).

Fotouhi, N., et al., "The Design and Synthesis of Potent Cyclic Peptide VCAM–VLA–4 Antagonists Incorporating an Achiral Asp–Pro Mimetic", *Bioorg. & Med. Chem. Lett.*, vol. 10, pp. 1171–1173 (2000).

Haubner, R., et al. "Cyclic RGD Peptides Containing β–Turn Mimetics." *J. Am. Chem. Soc.* 118: 7881–7891 (1996).

Hauptmann, J., et al. "Degradation of a Benzamidine–Type Synthetic Inhibitor of Coagulation Enzymes in Plasma of Various Species." *Thrombosis Research.* 61: 279–284 (1991).

Haworth, D., et al. "Anti–inflammatory activity of c(ILDV–NH(CH$_2$)$_5$CO), a novel, selective, cyclic peptide inhibitor of VLA–4–mediated cell adhesion." *Br. J. Pharmacol.* 126: 1751–1760 (1999).

Jackson, D.Y., et al., "Potent α4β1 Peptide Antagonists as Potential Anti–Inflammatory Agents", *J. Med. Chem.*, vol. 40, pp. 3359–3368 (1997).

Kato, Y., et al., "Oxidative Degradation of Collagen and Its Model Peptide by Ultraviolet Irradiation", *J. Agric. Food Chem.*, vol. 40, pp. 373–379 (1992).

Komoriya, A., et al. "The Minimal Essential Sequence for a Major Cell Type–specific Adhesion Site (CS1) within the Alternatively Spliced Type III Connecting Segment Domain of Fibronectin Is Leucine–Aspartic Acid–Valine." *J. Biol. Chem.* 266(23): 15075–15079 (1991).

Kudlacz, E., et al., "Pulmonary Eospinophilia in a Murine Model of Allergic Inflammation is Attenuated by Small Molecule α4β1 Antagonists", *J. of Pharm and Exp. Ther.*, vol. 301, No. 2, pp. 747–752.

Kurokawa, M., et al. "Synthesis and Antiinflammatory Activity of cis– and trans–6,6a,7,8,9,10,10a,11–Octahydro–11–oxodibenzo[b,e]thiepinacetic and –oxepinacetic Acids." *J. Med. Chem.* 33: 504–509 (1990).

Leibfritz, D., et al., *Tetrahedron* (1982), 38(14), 2165–81.

Lin, K., et al., "Selective, Tight–Binding Inhibitors of Integrin α4β1 that Inhibit Allergic Airway Responses", *J. Med. Chem.*, vol. 42, pp. 920–934.

Müller, G., et al., "Discovery and Evaluation of Piperidinyl Carboxylic Acid Derivatives as Potent $α_4β_1$ Integrin Antagonists", *Bioorg. & Med. Chem. Lett.*, ol. 11, pp. 3019–3021 (2001).

Papaioannou, D., et al., "Facile Preparation of the 1–Hydroxybenzotriazolyl Ester of N–Tritylpyroglutamic Acid and its Application to the Synthesis of TRH, [D–His$^2$] TRH and Analogues Incorporating cis– and trans–4–Hydroxy–L–Proline", *Acta Chem. Scand.*, vol. 49, pp. 103–114 (1995).

Peri, F., et al., "Assembly of Binding Loops on Aromatic Templates as VCAM–1 Mimetics", *J. of Peptide Sci.*, vol. 5, pp. 313–322 (1999).

Simanis, V. et al., *Int. J. Pept. Protein Res.* (1982), 19(1), 67–70.

Souers, A.J., et al., "Novel Inhibitors of α4β1 Integrin Receptor Interactions Through Library Synthesis and Screening", *Bioorg. & Med. Chem. Lett.*, vol. 8, pp. 2297–2302 (1998).

Tait, A., et al. "Synthesis and Antiinflammatory Activity of 2,6–Bis(1,1–Dimethylethyl)Phenol Derivatives." *(Il Farmaco.* 48(10): 1463–1473 (1993).

Uren, M.F., et al. "The Effect of Anti–Inflammatory Agents on the Clinical Expression of Bovine Ephemeral Fever." *Veterinary Microbiology.* 19: 99–111 (1989).

van der Laan, LJW, et al., "Beneficial Effect of Modified Peptide Inhibitor of α4 Integrins on Experimental Allergic Encephalomyelitis in Lewis Rats", *J. of Neurosci. Res.*, vol. 67, pp. 191–199 (2002).

Vatistas, N.J., et al. "Infection of the intertubercular bursa in horses: four cases (1978–1991)." *J. Am. Vet. Med. Assoc.* 208(9): 1434–1437 (1996).

Voigt, B., et al. "Synthese von Nα–(Arylsolfonyl–L–prolyl)–und Nα–Benzyloxycarbonyl–L–prolyl)–D,L–4–amidinophenyl–alaninamiden als Thrombininhibitoren." *Pharmazie.* 41: 233–235 (1986).

Yang, Y., et al. "LPAM–1 (integrin α4β7)–ligand binding: overlapping binding sites recognizing VCAM–1, Mad-CAM–1 and CS1 are blocked by fibrinogen, a fibronectin-like polymer and RGD–like cyclic peptides." *Eur. J. Immunol.* 28: 995–1004 (1998).

Chemical Abstract No. 126040, vol. 74, No. 23 (Jun. 7, 1971).

Chemical Abstract No. 176262, vol. 99, No. 21 (Nov. 21, 1983).

Chemical Abstract No. 210288, vol. 106, No. 25 (Jun. 22, 1987).

Chemical Abstract No. 167952, vol. 108, No. 19 (May 9, 1988).

Chemical Abstract No. 34164, vol. 125, No. 3 (Jul. 15, 1996).

Chemical Abstract No. 211689, vol. 117 (1992) Gamo.

* cited by examiner

ANTI-INFLAMMATORY COMPOSITIONS AND METHOD

This application claims the benefit of U.S. Provisional Application No. 60/112,020, which was converted pursuant to 37 C.F.R. §1.53(c)(2)(i) from U.S. patent application Ser. No. 08/904,424, filed Jul. 31, 1997 now abandoned and of U.S. Provisional Application No. 60/054,453, filed Aug. 1, 1997, all of which applications are incorporated herein by reference in their entireties.

FIELD OF THE INVENTION

The invention relates to compositions that modulate binding of a specific integrin molecule, $\alpha_9\beta_1$, to its receptor(s), to methods of treatment using such compounds, and to screening assays suitable for identifying additional modulatory compounds for use in such treatment methods. Pharmaceutical compositions which include such compounds are useful in treating inflammation and other disorders where modulation of $\alpha_9\beta_1$-receptor interactions is desirable.

REFERENCES

Hynes, R. O. (1987) Cell 48: 549–554.
Palmer, E. L., et al. (1993) J Cell Biol. 123: 1289–1297.
Smith, et al. (1996) J. Biol. Chem. 271: 28485.
Yednock, T. A., et al. J. Biol. Chem., 1995, 270: 28740–28750.
Yokosaki, et al. 1994, J. Biol. Chem. 269: 26691–26696.
Yokosaki, et al. 1996, J. Biol. Chem. 271: 24144–24150.

BACKGROUND OF THE INVENTION

The integrins are a group of glycoproteins that are present on a wide variety of cells, where they mediate cell-cell and cell-matrix adhesion via interactions with receptors present on cell membranes or in the extracellular matrix. Known receptors for the various integrin family members include cell surface immunoglobulins, extracellular matrix proteins (laminin, collagen, fibronectin, tenascin), and cadherins.

All known members of the integrin family are composed of two subunits, termed alpha and beta. There are currently at least sixteen recognized alpha subunits and eight different beta-subunits; integrins containing the $\beta_1$ form of the beta subunit are known as the "$\beta_1$ integrin family." Members of this family are expressed by a diverse distribution of tissues and exhibit specific binding specificities. Thus, $\alpha_1\beta_1$ integrin is expressed by T-lymphocytes and fibroblasts and binds to collagen and laminin; in contrast, $\alpha_4\beta_1$ integrin (VLA-4) is expressed by several types of hematopoietic cell and binds to VCAM-1, fibronectin and madCAM. It is therefore the alpha subunit that apparently confers receptor binding specificity to the protein.

A relatively new member of the $\beta_1$ integrin family, $\alpha_9\beta_1$ (also referred to herein as "alpha-9 integrin") has been shown to bind to tenascin and osteopontin, both of which are components of the extracellular matrix which are induced at sites of inflammation (Yokosaki; Smith). When sequences of the various alpha subunits were compared, alpha--9 integrin was shown to have the closest sequence identity to the alpha-4 subunit; however this represents only 39% sequence identity (Palmer). Moreover, the two subunits have different cell and tissue distributions. While $\alpha_9\beta_1$ is expressed on airway smooth muscle cells, and non-intestinal epithelial cells (Palmer), and diffusely on hepatocytes and basal keratinocytes (Yokosaki, 1994), $\alpha_4\beta_1$ integrin is present mainly on hematopoietic cells.

Heretofore, there has been no definitive determination of an in vivo function for $\alpha_9\beta_1$ integrin, nor has a physiological consequence of disruption of $\alpha_9\beta_1$-receptor interactions been identified, despite its presence in several tissues, as described above. Nor, despite its association with osteopontin and tenascin, has there been any reason to suspect that alpha-9 integrin might play a role in inflammatory disorders, since the $\alpha_9\beta_1$ molecule had not been associated with any of the hematopoietic cells commonly associated with this disorder.

In studies carried out in support of the present invention, it is now now found that $\alpha_9\beta_1$ is present on neutrophils, a class of phagocytic cells which play an important role in inflammation. In humans, these cells are notable for their relative lack of alpha-4/beta-1 integrin. Therefore, the present invention provides basis for involvement of $\alpha_9\beta_1$ in acute inflammatory responses.

Further differences among the $\beta_1$-integrins are associated with their binding specificities or endogenous ligands. While they all bind one or more proteins or proteoglycans that form the extracellular matrix, each integrin family member exhibits a distinct molecular specificity which may dictate, in part, its physiological specificity. Thus, while alpha-4/beta-1 integrin is known to bind fibronectin and VCAM-1, alpha-9 integrin has been characterized as binding the matrix proteins osteopontin and tenascin (Yokosaki, 1994; Smith, 1996). According to a further discovery related to the present invention, alpha-9 integrin also binds VCAM-1, though, as discussed below, it is likely that such binding occurs at a site that distinct from the alpha-4 binding site.

The present invention therefore provides basis for new therapeutic regimens directed at modulating alpha-9 integrin binding to its ligand(s), and in particular, those ligands which are involved in the inflammatory response. In addition, it is a further discovery of the present invention that many of the compounds or drugs that modulate (inhibit or enhance) alpha-4/beta-1 integrin binding also modulate alpha-9 integrin binding. This discovery therefore provides new pharmaceutical compositions and methods of treatment for modulating alpha-9 integrin binding, as well as screening methods for identifying new alpha-9 integrin modulatory compounds.

SUMMARY OF THE INVENTION

The invention is directed to pharmaceutical compositions and methods of treatment for disorders that involve binding of alpha-9 integrin, as well as screening assays that are useful in identifying compounds for use in such compositions and methods. More particularly, the invention is directed to inflammatory conditions, particularly those that involve increased adhesion macrophages or neutrophils, which, according to a discovery of the present invention, are now known to carry alpha-9 integrin in their membranes and to exhibit increased expression of alpha-9 integrin in response to stimulation by a known activator molecule, fMLP, as described herein.

A number of inflammatory disorders are therefore susceptible to treatment in accordance with the present invention, including but not limited to airway hyper-responsiveness and occlusion that occur in conjunction with chronic asthma, smooth muscle cell proliferation in atherosclerosis, vascular occlusion following angioplasty, fibrosis and glomerular scarring as a result of renal disease, aortic stenosis, hypertrophy of synovial membranes in rheumatoid arthritis, and inflammation and scarring that occur with the progression of ulcerative colitis, and Crohn's disease.

In preferred embodiments, pharmaceutical compositions and methods of treatment of the invention employ alpha-9 antagonist compounds that inhibit binding between alpha-9 integrin and an alpha-9 integrin ligand. Preferred ligands in this regard include any ligand found to specifically bind to alpha-9 integrin, as exemplified by osteopontin, tenascin, and VCAM-1. Due to its association with inflammatory reactions, VCAM-1 is particular preferred for a test compound in this regard.

In one embodiment, pharmaceutical compositions and treatment methods of the invention contain an alpha-9 integrin antagonist compound that exhibits a potency in inhibiting binding between alpha-9 integrin and an alpha-9 integrin ligand that is at least as high as 1/1000, and preferably at least as high as 1/100 of an inhibitory potency exhibited by a compound selected from the group consisting of nine reference compounds: N-(toluene-4-sulfonyl)-L-prolyl-L-4 (4-methylpiperazin 1-ylcarbonyloxy)phenylalanine, N-(toluene-4-sulfonyl)-L-prolyl-L-4(N,N-dimethylcarbamyloxy)phenylalanine, N-(1-methylpyrazole-4-sulfonyl)-L-prolyl-L-4-(N,N-dimethylcarbamyloxy) phenylalanine, N-(toluene-4-sulfonyl)-L-(1,1-dioxo-5,5-dimethyl)thiaprolyl-L-4-(N,N-dimethylcarbamyloxy) phenylalanine, N-(toluene-4-sulfonyl)-N-methyl-L-alaninyl-L-4-(N,N-dimethylcarbamyloxy)phenylalanine, N-(toluene-4-sulfonyl)-L-[1,1-dioxo)thiamorpholin-3-carbonyl]-L-4-(N,N-dimethylcarbamyloxy)phenylalanine, N-(N-p-toluenesulfonyl)prolyl-4-(piperazinoyloxy) phenylalanine, N-(N-p-toluenesulfonyl)sarcosyl-4-(N,N-dimethylcarbamyloxy) phenylalanine, and N-(toluene-4-sulfonyl)-L-(5,5-dimethyl)thiaprolyl-L-4-[3-(N,N-dimethyl)propoxy]phenylalanine.

The foregoing group of compounds are exemplary in nature, having been chosen for their relatively high potency in inhibiting alpha-9 integrin binding to an exemplary ligand, tenascin. The foregoing compounds also illustrate another aspect of the invention—that a rich source of candidate compounds for use in the pharmaceutical compositions and methods of treatment described herein is compounds known to inhibit binding or activity of alpha-4/beta-1 integrin (VLA-4). The foregoing 9 reference standard compounds can also be used in the pharmaceutical compositions and methods of treatment described above.

In another embodiment, pharmaceutical compositions and methods of treatment will employ alpha-9 integrin antagonists that have a $K_i$ or $IC_{50}$ (less than about 100 μM, as determined in an assay which measures inhibition of binding between alpha-9 integrin and an alpha-9 integrin ligand.

In another related embodiment, compounds useful in the pharmaceutical compositions and methods of treatment of the invention have the formula:

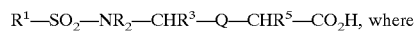

$R^1$—$SO_2$—$NR_2$—$CHR^3$—Q—$CHR^5$—$CO_2H$, where $R^1$ is selected from the group consisting of alkyl, substituted alkyl, aryl, substituted aryl, cycloalkyl, substituted cycloalkyl, heterocyclic, substituted heterocylic, heteroaryl and substituted heteroaryl;

$R^2$ is selected from the group consisting of hydrogen, alkyl, cycloalkyl, substituted cycloalkyl, cycloalkenyl, substituted cycloalkenyl, heterocyclic, substituted heterocyclic, substituted alkyl, aryl, substituted aryl, heteroaryl, substituted heteroaryl, and $R^1$ and $R^2$ together with the nitrogen atom bound to $R^2$ and the $SO_2$ group bound to $R^1$ can form a heterocyclic or a substituted heterocyclic group;

$R^3$ is selected from the group consisting of hydrogen, alkyl, substituted alkyl, cycloalkyl, substituted cycloalkyl, aryl, substituted aryl, heteroaryl, substituted heteroaryl, heterocyclic, substituted heterocyclic and, when $R^2$ does not form a heterocyclic group with $R^1$, $R^2$ and $R^3$ together with the nitrogen atom bound to $R^2$ and the carbon atom bound to $R^3$ can form a heterocyclic or a substituted heterocyclic group;

$R^5$ is —$(CH_2)_x$—Ar—$R^{5'}$ where $R^{5'}$ is selected from the group consisting of —O—Z—$NR^8R^8$ and —O—Z—$R^{12}$ wherein $R^8$ and $R^{8'}$ are independently selected from the group consisting of hydrogen, alkyl, substituted alkyl, cycloalkyl, substituted cycloalkyl, heterocyclic, substituted heterocyclic, and where $R^8$ and $R^{8'}$ are joined to form a heterocycle or a substituted heterocycle, $R^{12}$ is selected from the group consisting of heterocycle and substituted heterocycle, and Z is selected from the group consisting of —C(O)—and

—$SO_2$—,

Ar is aryl, heteroaryl, substituted aryl or substituted heteroaryl, x is an integer of from 1 to 4;

Q is —C(X)$NR^7$—wherein $R^7$ is selected from the group consisting of hydrogen and alkyl; and X is selected from the group consisting of oxygen and sulfur, and pharmaceutically acceptable salts thereof.

In still another related embodiment, the invention includes pharmaceutical compositions and methods which employ a small molecule compound. The compound is selected for its ability to inhibit binding between alpha-9 integrin and an alpha-9 integrin ligand, as evidenced by exhibiting a potency in an alpha-9 integrin-alpha-9 integrin ligand binding assay that is at least 1/1000 as high as a potency of a compound selected from the reference compound group listed above. In a related embodiment, such a compound is also an inhibitor of inhibitor of alpha-4/beta-1 integrin binding to VCAM-1, as evidenced by its ability to inhibit such binding with a potency that is at least 1/1000 as high as a potency exhibited by a compound selected from the reference standard group listed above. All pharmaceutical compositions and methods of treatment employ pharmaceutically effective dosages and are delivered in an excipient and manner appropriate to the particular treatment regimen selected by the practitioner.

According to a related aspect, the invention includes a method of screening for therapeutic compounds effective in treating conditions characterized by involvement of alpha-9 integrin, and in particular, inflammatory conditions, such as those listed above. The method includes adding test compound to an assay system which measures an amount of alpha-9 integrin binding to an alpha-9 integrin ligand, and selecting the test compound as an effective therapeutic drug candidate, if said compound exhibits a binding inhibitory activity that is at least 1/1000 as potent as an activity exhibited by a compound selected from the group of reference standard compounds listed above. Candidate compounds selected in this mode are further tested for safety and toxicity, according to methods well known in the art, prior to use in the pharmaceutical compositions and methods of treatment described herein.

Selection of test compounds for testing in the screening method is well within the skill of the practitioner in view of the wealth of combinatorial libraries now commerically available or available through the scientific literature. Nonetheless, in accordance with the present invention, particularly preferred test compounds are those known to exhibit activity in modulating, particularly inhibiting, binding between alpha-4/beta-1 integrin and any of its ligands, but particularly VCAM-1.

According to a preferred embodiment, an compound is selected by the assay if it exhibits an inhibitory potency that is at least as 1/1000 as high as an inhibitory potency exhibited by a compound selected from the reference standard group listed above. According to a related embodiment, preferred compounds are selected from a group having the formula: $R^1$—$SO_2$—$NR_2$—$CHR^3$—Q—$CHR^5$—$CO_2H$, where the substituent groups and moieties are defined as described above. These compounds are also described in co-owned parent applications U.S. patent application Ser. No. 08/904,424, filed Jul. 31, 1997, and U.S. Provisional Application No. 60/054,453, filed Aug. 1, 1997, which are incorporated herein by reference.

These and other objects and features of the invention will become more fully apparent when the following detailed description of the invention is read in conjunction with the accompanying drawings.

DETAILED DESCRIPTION OF THE INVENTION

I. Definitions

Figure 1:
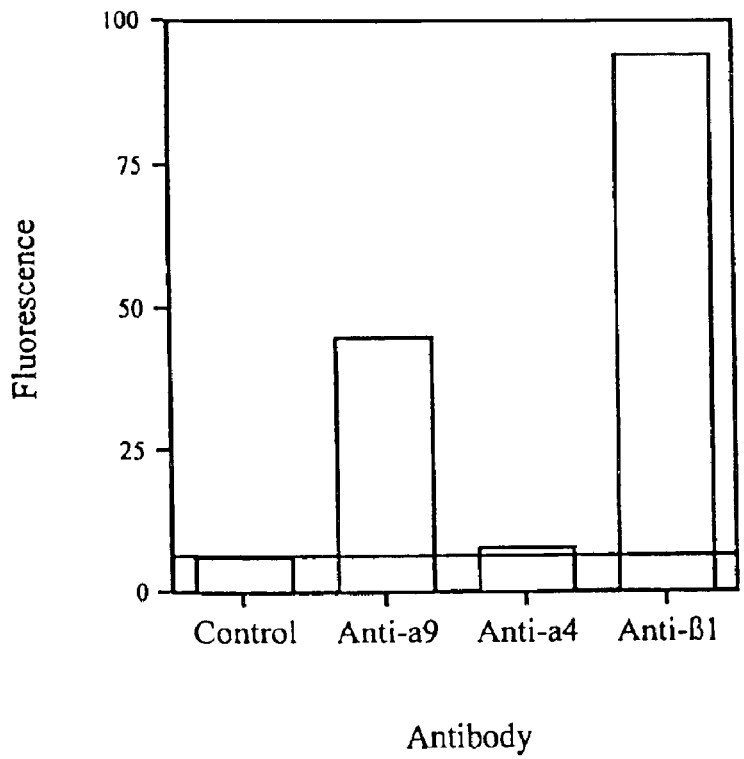
FIG. 1 shows a bar graph that illustrates expression of alpha-9 integrin on human neutrophils.

This section provides definitions of certain of the terms used herein. Unless specifically defined, all other scientific and technical terms used have the same meaning as commonly understood by one of ordinary skill in the art to which this invention belongs. A convenient reference for purposes the present invention is Stedman's Medical Dictionary 24$^{th}$ Edition (Williams and Wilkins, Baltimore)

As used herein, "alkyl" refers to alkyl groups preferably having from 1 to 10 carbon atoms and more preferably 1 to 6 carbon atoms. This term is exemplified by groups such as methyl, t-butyl, n-heptyl, octyl and the like.

"Substituted alkyl" refers to an alkyl group, preferably of from 1 to 10 carbon atoms, having from 1 to 5 substituents selected from the group consisting of alkoxy, substituted alkoxy, acyl, acylamino, thiocarbonylamino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxylaryl, substituted aryloxyaryl, cyano, halogen, hydroxyl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted aryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —$OS(O)_2$-alkyl, —$OS(O)_2$-substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$-substituted heterocyclic, —$OSO_2$—NRR where R is hydrogen or alkyl, —$NRS(O)_2$-alkyl, —$NRS(O)_2$-substituted alkyl, —$NRS(O)_2$-aryl, —$NRS(O)_2$-substituted aryl, —$NRS(O)_2$-heteroaryl, —$NRS(O)_2$-substituted heteroaryl, —$NRS(O)_2$-heterocyclic, —$NRS(O)_2$-substituted heterocyclic, —$NRS(O)_2$—NR-alkyl, —$NRS(O)_2$—NR-substituted alkyl, —$NRS(O)_2$—NR-aryl, —$NRS(O)_2$—NR-substituted aryl, —$NRS(O)_2$—NR-heteroaryl, —$NRS(O)_2$—NR-substituted heteroaryl, —$NRS(O)_2$—NR-heterocyclic, —$NRS(O)_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkyl groups having amino groups blocked by conventional blocking groups such as Boc, Cbz, formyl, and the like or alkyl/substituted alkyl groups substituted with —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-aryl, —$SO_2$-substituted aryl, —$SO_2$-heteroaryl, —$SO_2$-substituted heteroaryl, —$SO_2$-heterocyclic, —$SO_2$-substituted heterocyclic and —$SO_2NRR$ where R is hydrogen or alkyl.

"Alkoxy" refers to the group "alkyl-O—" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl-O—".

"Acyl" refers to the groups H-C(O)—, alkyl-C(O)—, substituted alkyl-C(O)—, alkenyl-C(O)—, substituted alkenyl-C(O)—, alkynyl-C(O)—, substituted alkynyl-C(O)— cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acylamino" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thiocarbonylamino" refers to the group —C(S)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form, together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl group preferably having from 2 to 10 carbon atoms and more preferably 2 to 6 carbon atoms and having at least 1 and preferably from 1–2 sites of alkenyl unsaturation.

"Substituted alkenyl" refers to alkenyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS-(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS-(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkynyl" refers to alkynyl group preferably having from 2 to 10 carbon atoms and more preferably 3 to 6 carbon atoms and having at least 1 and preferably from 1–2 sites of alkynyl unsaturation.

"Substituted alkynyl" refers to alkynyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS-(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS-(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Amidino" refers to the group

and the term "alkylamidino" refers to compounds having 1 to 3 alkyl groups

"Thioamidino" refers to the group

where R is hydrogen or alkyl.

Aminoacyl" refers to the groups —NRC(O)alkyl, —NRC(O)substituted alkyl, —NRC(O)cycloalkyl, —NRC(O) substituted cycloalkyl, —NRC(O)alkenyl, —NRC(O) substituted alkenyl, —NRC(O)alkynyl, —NRC(O) substituted alkynyl, —NRC(O)aryl, —NRC(O)substituted aryl, —NRC(O)heteroaryl, —NRC(O)substituted heteroaryl, —NRC(O)heterocyclic, and —NRC(O) substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the groups —NRC(O)O-alkyl, —NRC(O)O-substituted alkyl, —NRC(O)O-alkenyl, —NRC(O)O-substituted alkenyl, —NRC(O)O-alkynyl, —NRC(O)O-substituted alkynyl, —NRC(O)O-cycloalkyl, —NRC(O)O-substituted cycloalkyl, —NRC(O)O-aryl, —NRC(O)O-substituted aryl, —NRC(O)O-heteroaryl, —NRC(O)O-substituted heteroaryl, —NRC(O)O-heterocyclic, and —NRC(O)O-substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxycarbonylamino" refers to the groups —OC(O)NH$_2$, —OC(O)NRR, —OC(O)NR-alkyl, —OC(O)NR-substituted alkyl, —OC(O)NR-alkenyl, —OC(O)NR-substituted alkenyl, —OC(O)NR-alkynyl, —OC(O)NR-substituted alkynyl, —OC(O)NR-cycloalkyl, —OC(O)NR-substituted cycloalkyl, —OC(O)NR-aryl, —OC(O)NR-substituted aryl, —OC(O)NR-heteroaryl, —OC(O)NR-substituted heteroaryl, —OC(O)NR-heterocyclic, and —OC(O)NR-substituted heterocyclic where R is hydrogen, alkyl or where each R is joined to form, together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxythiocarbonylamino" refers to the groups —OC(S)NH$_2$, —OC(S)NRR, —OC(S)NR-alkyl, —OC(S)NR-substituted alkyl, —OC(S)NR-alkenyl, —OC(S)NR-substituted alkenyl, —OC(S)NR-alkynyl, —OC(S)NR-substituted alkynyl, —OC(S)NR-cycloalkyl, —OC(S)NR-substituted cycloalkyl, —OC(S)NR-aryl, —OC(S)NR-substituted aryl, —OC(S)NR-heteroaryl, —OC(S)NR-substituted heteroaryl, —OC(S)NR-heterocyclic, and —OC(S)NR-substituted heterocyclic where R is hydrogen, alkyl or where each R is joined to form together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the groups —NRC(O)NRR, —NRC(O)NR-alkyl, —NRC(O)NR-substituted alkyl, —NRC(O)NR-alkenyl, —NRC(O)NR-substituted alkenyl, —NRC(O)NR-alkynyl, —NRC(O)NR-substituted alkynyl, —NRC(O)NR-aryl, —NRC(O)NR-substituted aryl, —NRC(O)NR-cycloalkyl, —NRC(O)NR-substituted cycloalkyl, —NRC(O)NR-heteroaryl, and —NRC(O)NR-substituted heteroaryl, —NRC(O)NR-heterocyclic, and —NRC(O)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the groups —NRC(S)NRR, —NRC(S)NR-alkyl, —NRC(S)NR-substituted alkyl, —NRC(S)NR-alkenyl, —NRC(S)NR-substituted alkenyl, —NRC(S)NR-alkynyl, —NRC(S)NR-substituted alkynyl, —NRC(S)NR-aryl, —NRC(S)NR-substituted aryl, —NRC(S)NR-cycloalkyl, —NRC(S)NR-substituted cycloalkyl, —NRC(S)NR-heteroaryl, and —NRC(S)NR-substituted heteroaryl, —NRC(S)NR-heterocyclic, and —NRC(S)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to an unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7yl, and the like). Preferred aryls include phenyl and naphthyl.

Substituted aryl refers to aryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxyamido, cyano, thiol, thioalkyl, substituted thioalkyl, thioaryl. substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Aryloxy" refers to the group aryl-O— which includes, by way of example, phenoxy, naphthoxy, and the like.

"Substituted aryloxy" refers to substituted aryl-O— groups.

"Aryloxyaryl" refers to the group -aryl-O-aryl.

"Substituted aryloxyaryl" refers to aryloxyaryl groups substituted with from 1 to 3 substituents on either or both aryl rings selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxyamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Cycloalkyl" refers to cyclic alkyl groups of from 3 to 8 carbon atoms having a single cyclic ring including, by way of example, cyclopropyl, cyclobutyl, cyclopentyl, cyclooctyl and the like. Excluded from this definition are multi-ring alkyl groups such as adamantanyl, etc.

"Cycloalkenyl" refers to cyclic alkenyl groups of from 3 to 8 carbon atoms having a single cyclic ring.

"Substituted cycloalkyl" and "substituted cycloalkenyl" refers to an cycloalkyl or cycloalkenyl group, preferably of from 3 to 8 carbon atoms, having from 1 to 5 substituents selected from the group consisting of oxo (═O), thioxo (═S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxylcycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS- (O)₂-substituted aryl, —OS(O)₂-heteroaryl, —OS(O)₂-substituted heteroaryl, —OS(O)₂-heterocyclic, —OS(O)₂-substituted heterocyclic, —OSO₂—NRR where R is hydrogen or alkyl, —NRS(O)₂-alkyl, —NRS(O)₂-substituted alkyl, —NRS(O)₂-aryl, —NRS(O)₂-substituted aryl, —NRS(O)₂-heteroaryl, —NRS(O)₂-substituted heteroaryl, —NRS(O)₂-heterocyclic, —NRS(O)₂-substituted heterocyclic, —NRS(O)₂—NR-alkyl, —NRS(O)₂—NR-substituted alkyl, —NRS(O)₂—NR-aryl, —NRS(O)₂—NR-substituted aryl, —NRS(O)₂—NR-heteroaryl, —NRS-(O)₂—NR-substituted heteroaryl, —NRS(O)₂—NR-heterocyclic, —NRS(O)₂—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO₂-alkyl, —SO₂-substituted alkyl, —SO₂-alkenyl, —SO-substituted alkenyl, —SO₂-cycloalkyl, —SO₂-substituted cycloalkyl, —SO₂-aryl, —SO₂-substituted aryl, —SO₂-heteroaryl, —SO₂-substituted heteroaryl, —SO₂-heterocyclic, —SO₂-substituted heterocyclic and —SO₂NRR where R is hydrogen or alkyl.

"Cycloalkoxy" refers to —O-cycloalkyl groups.

"Substituted cycloalkoxy" refers to —O-substituted cycloalkyl groups.

"Guanidino" refers to the groups —NRC(=NR)NRR, —NRC(=NR)NR-alkyl, —NRC(=NR)NR-substituted alkyl, —NRC(=NR)NR-alkenyl, —NRC(=NR)NR-substituted alkenyl, —NRC(=NR)NR-alkynyl, —NRC(=NR)NR-substituted alkynyl, —NRC(=NR)NR-aryl, —NRC(=NR)NR-substituted aryl, —NRC(=NR)NR-cycloalkyl, —NRC(=NR)NR-heteroaryl, —NRC( NR)NR-substituted heteroaryl, —NRC(=NR)NR-heterocyclic, and —NRC(=NR)NR-substituted heterocyclic where each R is independently hydrogen and alkyl as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Guanidinosulfone" refers to the groups —NRC(=NR)NRSO₂-alkyl, —NRC(=NR)NRSO₂-substituted alkyl, —NRC(=NR)NRSO₂-alkenyl, —NRC(=NR)NRSO₂-substituted alkenyl, —NRC(=NR)NRSO₂-alkynyl, —NRC(=NR)NRSO₂-substituted alkynyl, —NRC(=NR)NRSO₂-aryl, —NRC(=NR)NRSO₂-substituted aryl, —NRC(=NR)NRSO₂-cycloalkyl, —NRC(=NR)NRSO₂-substituted cycloalkyl, —NRC(=NR)NRSO₂-heteroaryl, and —NRC(=NR)NRSO₂-substituted heteroaryl, —NRC(=NR)NRSO₂-heterocyclic, and —NRC(=NR)NRSO₂-substituted heterocyclic where each R is independently hydrogen and alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Halo" or "halogen" refers to fluoro, chloro, bromo and iodo and preferably is either chloro or bromo.

"Heteroaryl" refers to an aromatic carbocyclic group of from 2 to 10 carbon atoms and 1 to 4 heteroatoms selected from oxygen, nitrogen and sulfur within the ring. Such heteroaryl groups can have a single ring (e.g., pyridyl or furyl) or multiple condensed rings (e.g., indolizinyl or benzothienyl). Preferred heteroaryls include pyridyl, pyrrolyl, indolyl and furyl.

"Substituted heteroaryl" refers to heteroaryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)₂-alkyl, —S(O)₂-substituted alkyl, —S(O)₂-cycloalkyl, —S(O)₂-substituted cycloalkyl, —S(O)₂-alkenyl, —S(O)₂-substituted alkenyl, —S(O)₂-aryl, —S(O)₂-substituted aryl, —S(O)₂-heteroaryl, —S-(O)₂-substituted heteroaryl, —S(O)₂-heterocyclic, S(O)₂-substituted heterocyclic, —OS(O)₂-alkyl, —OS(O)₂-substituted alkyl, —OS(O)₂-aryl, —OS(O)₂-substituted aryl, —OS(O)₂-heteroaryl, —OS(O)₂-substituted heteroaryl, —OS(O)₂-heterocyclic, —OS(O)₂-substituted heterocyclic, —OSO₂—NRR where R is hydrogen or alkyl, —NRS(O)₂-alkyl, —NRS(O)₂-substituted alkyl, —NRS-(O)₂-aryl, —NRS(O)₂-substituted aryl, —NRS(O)₂-heteroaryl, —NRS(O)₂-substituted heteroaryl, —NRS(O)₂-heterocyclic, —NRS(O)₂-substituted heterocyclic, —NRS(O)₂—NR-alkyl, —NRS(O)₂—NR-substituted alkyl, —NRS(O)₂-NR-aryl, —NRS(O)₂—NR-substituted aryl, —NRS(O)₂—NR-heteroaryl, —NRS(O)₂—NR-substituted heteroaryl, —NRS(O)₂—NR-heterocyclic, —NRS(O)₂—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO₂NRR where R is hydrogen or alkyl.

"Heteroaryloxy" refers to the group —O-heteroaryl and "substituted heteroaryloxy" refers to the group —O-substituted heteroaryl.

"Heterocycle" or "heterocyclic" refers to a saturated or unsaturated group having a single ring or multiple condensed rings, from 1 to 10 carbon atoms and from 1 to 4 hetero atoms selected from nitrogen, sulfur or oxygen within the ring wherein, in fused ring systems, one or more the rings can be aryl or heteroaryl.

"Substituted heterocyclic" refers to heterocycle groups which are substituted with from 1 to 3 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxylcycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS-(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS-(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholino, thiomorpholino, piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic.

"Thiol" refers to the group —SH.

"Thioalkyl" refers to the groups —S-alkyl

"Substituted thioalkyl" refers to the group —S-substituted alkyl.

"Thiocycloalkyl" refers to the groups —S-cycloalkyl.

"Substituted thiocycloalkyl" refers to the group —S-substituted cycloalkyl.

"Thioaryl" refers to the group —S-aryl and "substituted thioaryl" refers to the group —S-substituted aryl.

"Thioheteroaryl" refers to the group —S-heteroaryl and "substituted thioheteroaryl" refers to the group —S-substituted heteroaryl.

"Thioheterocyclic" refers to the group —S-heterocyclic and "substituted thioheterocyclic" refers to the group —S-substituted heterocyclic.

"Pharmaceutically acceptable salt" refers to pharmaceutically acceptable salts of a compound of Formula I/IA which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "alpha-9 integrin" refers to a heterodimeric protein member of the $\beta_1$ integrin family which is also referred to as $\alpha_9\beta_1$.

The term "alpha-9 integrin ligand" refers to molecules to which alpha-9 integrin binds in vitro or preferably in vivo. Preferably, such binding occurs with a binding affinity or potency in the range of at least about $10^{-4}$ M and typically between about $10^{-5}$ to $10^{-8}$ M. The term also refers to fragments of such compounds that possess such binding affinity characteristics. Exemplary alpha-9 integrin ligands include, but are not limited to tenascin, osteopontin, and VCAM-1.

The term "binding affinity" as used herein refers to the relative strength with which two or more molecules bind together. In its usage herein, the term is typically expressed in terms of the molar amount of compound necessary to observe a desired effect, such as ½ maximal binding or response ($EC_{50}$ or $K_d$), or inhibition of binding ($IC_{50}$ or $K_i$), but may also be used in a relative sense to express an amount of compound required to observe minimal saturation of a ligand, such as in the integrin saturation assays described herein.

The term "potency" is generally used to refer to relative affinities or efficacies; a compound has a "higher potency" than another if it is more effective than a reference compound when the two are compared at the same molar concentration, or if it produces the same effect at a lower concentration. The term may also be used to compare amounts of different compound needed to observe an arbitrary effect. By way of example, a test compound is said exhibits "a potency that is at least as high as 1/1000 of a reference standard potency, if it produces the same effect as the reference standard at no more than 1000 times the molar concentration required for the reference standard. Therefore, if the reference standard produces a given effect at a concentration of 1 µM, a test compound would be at least 1/1000 as potent if it is capable of producing the same effect at any concentration less than 1000 µM (1 mM).

The term "pharmaceutical composition" refers to a pharmaceutically active preparation of drug or biological which is prepared in a pharmaceutical excipient, such as buffered saline or a physiological buffer appropriate for administration to a subject. Appropriate excipients, including but not limited to diluents, fillers and the like are formulated based on the anticipated mode of administration and are readily determined by persons skilled in the art.

The term "small molecule" generally refers to an organic compound having a molecular weight that is less than about 2000 and preferably less than about 1000; small molecules may include short peptides and peptidomimetics.

The term "alpha-4/beta-1 integrin" refers to a heterodimeric protein which is also referred to as $\alpha_4\beta_1$ and as VLA-4.

The term "alpha-4/beta-1 integrin ligand" refers to molecules to which alpha-4/beta-1 integrin binds in vitro or preferably in vivo. Preferably, such binding occurs with a binding affinity in the range of at least about $10^{-4}$ M and typically between about $10^{-5}$ to $10^{-8}$ M. The term also refers to fragments of such compounds that possess such binding affinity characteristics. Exemplary alpha-4/beta-1 integrin ligands include, but are not limited to fibronectin (HEPII and CS1 domains), VCAM-1, osteopontin, and madCAM1. Generally, such ligands include a peptide binding site having the sequence EILDV.

The term "condition associated with binding of alpha-9 integrin to an alpha-9 integrin ligand" describes conditions having attributes consistent with the presence of increased or reduced alpha-9 integrin bound to an endogenous alpha-9 integrin ligand as compared to normal. An example of increased alpha-9 integrin binding is increased adhesion of neutrophils to osteopontin or tenascin, or another alpha-9 ligand during inflammation. In view of studies carried out in support of the present invention and described herein, alpha-9 integrin is likely to be involved in such increased adherence. Thus inflammation is considered a condition associated with binding of alpha-9 integrin.

An "alpha-9 integrin modulatory compound" or an "alpha-9 integrin regulatory compound" is a compound, preferably but not necessarily a small molecule, which, when added to a mixture which contains alpha-9 integrin and an alpha-9 integrin ligand, affects the binding between the integrin molecule and the ligand—for example, by producing an increase or decrease of such binding. By way of example, a modulatory compound which inhibits or reduces alpha-9 integrin binding to tenascin is referred to as an alpha-9 antagonist.

An effect or response is "significantly different," "significantly higher" or "significantly lower" if, when compared to an appropriate control, the test response shows a statistically significant change, when analyzed by an appropriate statistical method. In general, when it is stated that a response or effect is increased or decreased, it can be inferred that the observed increase or decrease is statistically significant or is expected to be statistically significant when subjected to appropriate experimental analysis.

Common amino acids are referred to by their one- or three-letter abbreviations as follows: alanine (A, Ala), cysteine (C, Cys), aspartic acid (D, Asp), glutamic acid (E, Glu), phenylalanine (F, Phe), glycine (G, Gly), histidine (H, His), isoleucine (I, Ile), lysine (K, Lys), leucine (L, Leu), methionine (M, Met), asparagine (N, Asn), proline (P, Pro), glutamine (Q, Gln), arginine (R, Arg), serine (S, Ser), threonine (T, Thr), valine (V, Val), tryptophan (W, Trp), tyrosine (Y, Tyr).

II. Alpha-9 Integrin

This section provides further background information about alpha-9 integrin, including means for distinguishing it from other integrins. Such distinguishing means are important in (i) setting up assays capable of measuring binding or blockade of binding between $\alpha_9\beta_1$ integrin and its ligand(s), and (ii) identifying compounds that are preferably small molecule antagonists capable of blocking interactions between $\alpha_9\beta_1$ integrin and its ligands(s).

A. Physical Characteristics

As mentioned above, $\alpha_9\beta_1$ integrin is a heterodimeric protein consisting of an alpha-subunit, termed $\alpha_9$ (or "alpha-9"), and a beta-subunit, generally $\beta_1$ (or "beta-1"). The two subunits bind to one another noncovalently, and each consists of a relatively short carboxy terminal intracellular domain which contains the highly conserved sequence GFF (R/K)R, a single transmembrane domain and a relatively large amino terminus extracellular domain which generally projects on the surface of cells.

The deduced amino acid sequence of the alpha-9 subunit has been determined by cloning (Palmer, 1993; GENBANK Accession No. L24158) The human alpha-9 subunit is a protein of 1006 amino acids. Studies comparing the various forms of alpha subunits have revealed that the alpha-9 subunit exhibits only 39% sequence identity with the alpha-4 integrin subunit.

B. Tissue Localization and Binding Selectivity of alpha-9 Integrin $\alpha_9\beta_1$ integrin is expressed by a number of different cell types, as mentioned above. For example, $\alpha_9\beta_1$ is found on airway smooth muscle cells, and non-intestinal epithelial cells, as well as a teratoma cell line (Palmer), and diffusely on hepatocytes and basal keratinocytes (Yokosaki, 1994). Heretofore, alpha-9 has not been shown to be present on any of the hematopoietic cells.

FIG. 1 shows results of experiments carried out in support of the present invention that show that, in addition to the previously known tissue distribution described above, alpha-9 integrin is also expressed by human neutrophils. In this experiment, alpha-9 subunit, alpha-4 subunit and beta-1 subunit were measured after reacting human neutrophils with fluorescently labeled antibodies specifically reactive with each of the foregoing subunits. This shows that, surprisingly, human neutrophils express alpha-9 subunit along with beta-1 subunit, and confirms that they express very little, if any alpha-4 subunit.

Neutrophils are phagocytic blood cells that are involved in a number of inflammatory conditions, particularly acute inflammation, as described below. These cells were previously distinguished by their lack of alpha-4/beta-1 integrin, which is expressed by all, or nearly all other circulating leucocytes.

Figure 2:
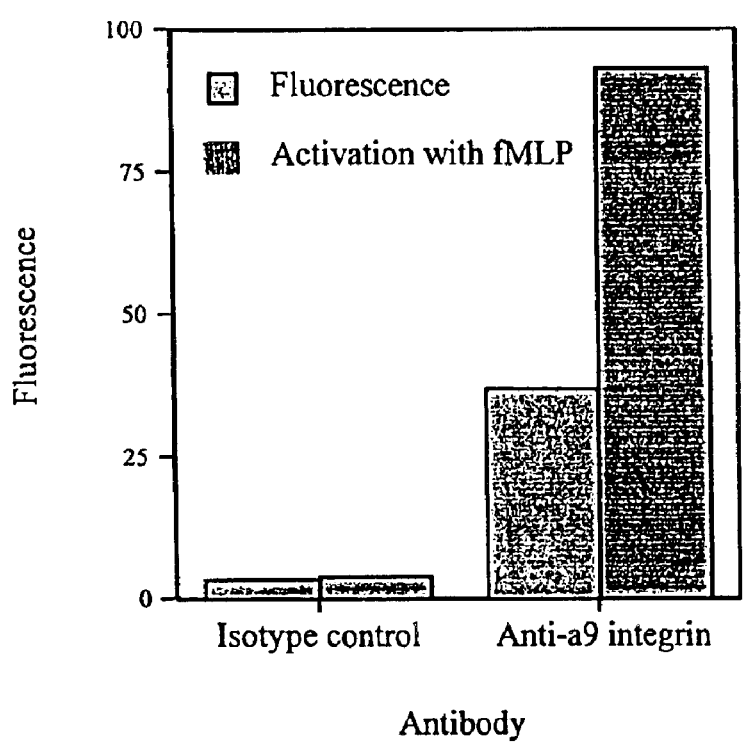
FIG. 2 shows a bar graph illustrating selective enhancement of expression of alpha-9 integrin ("anti-a9 integrin) as compared to control ("isotype control") on human neutrophils following activation by fMLP (right-hand bars).

Further experiments in support of the invention indicated that alpha-9 integrin is likely involved in inflammatory responses involving neutrophils. Formyl-Met-Leu-Phe (fMLP) is an activation factor that is involved in inflammation. FIG. 2 is a bar graph that shows that alpha-9 integrin expression is significantly and selectively increased following activation by fMLP (right-hand bars), as compared to a control idiotype-specific marker. This increased expression is consistent with alpha-9 involvement in activation of neutrophils during inflammation.

Studies on the binding selectivity of alpha-9 integrin have revealed that the molecule binds to tenascin at a "fibrinogen-like" type-III repeat (termed "TNfn3"). Although this region of tenascin contains the characteristic "RGD" (Arg-Gly-Asp) peptide binding site to which other integrins $\alpha_8\beta_1$, $\alpha_v\beta_3$, and $\alpha_v\beta_6$) preferentially bind, this is apparently not the site bound by alpha-9 integrin (Yokosaki, 1994). Rather, $\alpha_9\beta_1$ integrin binds preferentially to the B-C loop which contains the peptide sequence AEIDGIEL, and a peptide containing this sequence has been shown to disrupt binding between cells expressing alpha-9 integrin and TNFn3 (Yokosaki, 1998).

III. Alpha-9 Integrin Modulatory Compounds

This section provides guidance for identifying compounds for use as alpha-9 integrin modulatory compounds suitable for use in pharmaceutical compositions and treatment methods in accordance with the present invention. Specifically, in studies carried out in support of the present invention it has been found that, despite their sequence and ligand binding site dissimilarities noted above, alpha-4/beta-1 integrin and alpha-9 integrin apparently share similar binding sites for small molecules, and that binding to such sites serves to similarly modulate their abilities to bind to endogenous ligands.

Therefore, according to a preferred aspect of the present invention, compounds that modulate alpha-4/beta-1 integrin binding to its ligands are likely to also have activity in alpha-9 integrin assays. Accordingly, as described below, a rich source of compounds for testing in specific alpha-9 integrin modulatory assays consists of small molecules, including peptides and peptidomimetics, that have been characterized as alpha-4/beta-1 integrin agonists or antagonists. Further candidate compounds are provided by a variety of libraries, including, without limitation, combinatorial libraries, fermentation broths and lysates, phage libraries, and the like, such as are well known in the art and/or commercially available for screening, as discussed in more detail in Part B, below. Such libraries of compounds, in addition to the alpha-4/beta-1 modulatory compounds mentioned above and any other compounds can be conveniently screened in assay formats known in the art with reference to the exemplary assays described herein. Such assays can be further modified to accommodate high throughput screening of compounds according to methods known in the art.

A. Alpha-4/beta-1 integrin Agonists and Antagonists

In contrast to alpha-9 integrin, which has only recently been characterized, alpha-4/beta-1 integrin has been widely studied and has been the focus of numerous drug development programs. Alpha-4/beta-1 integrin is expressed by most forms of hematopoeitic cells, with the exception of neutrophils (e.g., $\alpha_4\beta_1$ is expressed by T- and B-lymphocytes, monocytes and certain antigen presenting cells). Alpha-4/beta-1 integrin binds endogenous ligands including fibronectin, mucosal addressin (MadCAM-1), vascular cell adhesion molecule-1 (VCAM-1; Cd106) and osteopontin. In particular, its interaction with VCAM-1, which is induced in the vascular epithelium during acute inflammatory responses, its presence on leukocytes, and its recognized involvement in the enhanced adhesion of such leukocytes at sites of inflammation have made $\alpha_4\beta_1$ a target for compounds in development for treatment of a variety of inflammatory diseases, including rheumatoid arthritis, heart disease and ulcerative colitis, among others.

Studies carried out in support of the present invention have revealed that compounds which modulate binding of alpha-4/beta-1 integrin to any of its ligands, including VCAM-1, are generally also good candidates for modulating binding of alpha-9 integrin to its ligand(s). More specifically, as described in section IV, below, specific antagonists of alpha-4/beta-1 integrin also block alpha-9 integrin binding to tenascin. This discovery therefore provides a wealth of candidate compounds for use in pharmaceutical compositions and methods of the present invention. For example, co-owned, concurrently-filed application U.S. Ser. No. 09/126,958, (PCT Serial No. PCT/US98/15324) incorporated herein by reference, which claims priority to the same initial U.S. patent applications, U.S. patent application Ser. No. 08/904,424, filed Jul. 31, 1997, and U.S. Provisional Application No. 60/054,453, filed Aug. 1, 1997, which are incorporated herein by reference in their entireties, describes a series of carbamyloxy compounds which have been characterized as inhibitors of alpha-4/beta-1 integrin binding to its ligands (i.e., $\alpha_4\beta_1$ antagonists). Testing and use of several exemplary compounds of this series are discussed below. Methods for making such compounds are detailed in Example 4 herein.

Similarly, co-owned U.S. patent applications U.S. Ser. No. 08/904,415, U.S. Ser. No. 08/903,585, U.S. Ser. No. 08/904,423, U.S. Ser. No. 08/920,353, U.S. Ser. No. 08/904,417, U.S. Ser. No. 08/920,394 and U.S. Ser. No. 08/904,416, all filed on Jul. 31, 1997, describe additional, structurally distinct alpha-4/beta-1 integrin antagonists which inhibit binding of alpha-4/beta-1 integrin to its ligand(s). The foregoing applications are hereby incorporated herein by reference for their teachings of such compounds which, in accordance with the present invention, are also candidates for use in the pharmaceutical compositions and methods of treatment that are the subjects of the present invention. In view of the data presented below, is anticipated that many of these compounds will exhibit approximately equipotent inhibitory activities in inhibiting alpha-9 integrin as in inhibiting alpha-4/beta-1 integrin.

B. Sources of Test Compounds

Additional sources of candidate alpha-9 integrin modulatory compounds are therefore apparent, in view of the discovery that at least a significant subset of alpha-4/beta-1 (VLA-4) inhibitory compositions may be active as alpha-9 integrin antagonists. That is, persons skilled in the art will recognize that compounds that are characterized as inhibiting or enhancing alpha-4/beta-1 integrin binding to its ligand(s) are strong candidates for modulating alpha-9 integrin binding to its respective ligands. Therefore, it will be a relatively routine matter, in view of the teaching of the present invention, to identify candidate compounds, for example, by conducting database searches of the patent or chemical literature for alpha-4/beta-1 (VLA-4) inhibitory compositions. Exemplary methods for further testing such compounds (e.g., for specificity and selectivity of binding, as well as for relative binding affinity) are provided in Section IV below.

With the advent of automated, high throughput screening procedures and the development of a variety of forms of combinatorial chemical libraries, persons skilled in the art will recognize that it will be relatively routine to identify additional alpha-9 modulatory compounds, in view of the guidance for selecting such compounds that is provided herein. For example, but not by way of limitation to the invention, random libraries are a rich source of materials. Moreover, combinatorial libraries can be produced for many types of compounds that can be synthesized in a step-by-step fashion. Such compounds include peptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608. Affymax. WP 0306121, Columbia University WO 94/08051, Pharmacopeia, WO 95/35503, and Scripps WO 95/30642 (each of which is incorporated herein by reference for all purposes). Peptide libraries can also be generated by phage display methods. See e.g., Devlin, WO 91/18980, incorporated herein by reference.

Combinatorial libraries and other compounds are initially screened by testing in an alpha-9 integrin activity assay, such as one or more of the assays described herein, and a compound is selected for use in the pharmaceutical compositions and methods of the invention if it satisfies the criteria set forth, particularly in Section IV, herein.

C. Compositions Including Alpha-9 Integrin Modulatory Compounds

Test compounds, preferably, but not necessarily selected as described above and tested as described below are further considered for use in pharmaceutical compositions of the present invention if they exhibit a potency in an alpha-9 integrin assay that is comparable to threshold activities determined by certain reference compounds, as discussed below. Such compositions will be suitable for further use in pharmaceutical compositions, subject to testing in an appropriate in vivo model appropriate to the specific target disorder and subject to appropriate tests of safety for the mammalian species to be treated. Appropriate dosages to be delivered will be estimated according to standard pharmacokinetic analyses, as discussed in Section V, below. As a general guideline, an effective dosage of a compound will be that amount of compound which is effective to produce a significant biochemical effect in the target tissue, with reference to the effective concentrations determined from in vitro or in vivo assays, such as are discussed below.

IV. Screening Assays for Compounds that Regulate Alpha-9 Integrin Binding

As mentioned above, a highly enriched source of compounds suitable for inclusion in the pharmaceutical compositions and methods of treatment of the present invention are compounds that are identified as alpha-4/beta-1 integrin antagonists. Such compounds are identified, either with reference to the scientific and patent literature or by empirical testing in an alpha-4/beta-1 integrin binding assay, as exemplified in Part A below. Part B describes exemplary alpha-9 integrin activity assays that provide information on alpha-9 integrin modulatory compounds in accordance with the present invention.

A. Alpha-4/beta-1 Integrin Binding and Activity Assays

Assays and test systems for determining whether a test compound is active in binding to and modulating activity of alpha-4/beta-1 integrin are well known in the art. By way of example, but not limitation, such assays include in vitro assays which measure the ability of alpha-4/beta-1 integrin present on cells known to bind to one or more of its ligands, such as VCAM-1. An exemplary cell-soluble VCAM-1 protein assay suitable for this purpose is detailed in Example 1 herein, and is also described further in the parent applications, U.S. patent application Ser. No. 08/904,424, filed Jul. 31, 1997, and U.S. Provisional Application No. 60/054,453, filed Aug. 1, 1997, both of which are incorporated herein in their entireties. These documents also describe results that identify several hundred effective alpha-4/beta-1 integrin antagonist compounds in this assay.

Briefly, in order to test compounds in this assay, compounds are synthesized, obtained from commercial sources, including a screening library, as discussed in Section III, above. In experiments carried out in support of the present invention, compounds were synthesized, for example, as detailed in Example 4 herein. Test compounds are then added to the screening assay, incubated, and the amount of binding between alpha-4/beta-1 integrin and its ligand, for example, VCAM-1, is measured as detailed in Example 1.

By way of example, an appropriate assay for measuring this interaction employs an antibody which binds to an activation/ligand-induced epitope on the beta-1 subunit. It therefore binds only to ligand activated cells and can therefore be used as a measure of how much ligand is bound (or, conversely, displaced) in the presence of test compound.

Briefly, in experiments carried out in support of the present invention, the activity of $\alpha 4\beta 1$ integrin was measured by the interaction of soluble VCAM-1 with a human T-cell line (Jurkat) which expresses high levels of $\alpha 4\beta 1$ integrin. Recombinant soluble VCAM-1 was expressed as a chimeric fusion protein containing the seven extracellular domains of VCAM-1 on the N-terminus and the human IgG1 heavy chain constant region on the C-terminus. The detector antibody, termed "15/7" was raised as a monoclonal antibody against immunopurified $\alpha_4\beta_1$ integrin and was selected on the basis of surface reactivity with U937 cells (ATCC; CRL 1593), then screened for differential reactivity with Jurkat and THP-1 cells (ATCC; TIB-202). This antibody was further characterized to have the reactivity described above (Yednock). Antibodies similar to the 15/7 antibody have been prepared by other investigators (Luque, et al, 1996, *J. Bio. Chem.* 271:11067) and may be used in this assay.

Jurkat cells were incubated with $Mn^{2+}$ and 15/7 antibody on ice. Mn+2 activates the receptor to enhance ligand binding, and 15/7 recognizes an activated/ligand occupied conformation of $\alpha 4\beta 1$ integrin and locks the molecule into this conformation thereby stabilizing the VCAM-1/$\alpha 4\beta 1$ integrin interaction. Cells were then incubated for 30 minutes at room temperature with candidate compounds, in various concentrations using a standard 5-point serial dilution. Soluble recombinant VCAM-1 fusion protein was then added to Jurkat cells and incubated for 30 minutes on ice. Cells were then washed two times and resuspended in PE-conjugated goat F(ab')2 anti-mouse IgG Fc (Immunotech, Westbrook, Me.) incubated on ice, in the dark, for 30 minutes. Cells were washed twice and analyzed with a standard fluorescence activated cell sorter ("FACS") analysis as described in Yednock, et al., supra. Compounds having an $IC_{50}$ of less than about 1 mM, and preferably less than about 100 $\mu$M possess sufficient binding activity to be considered for further testing.

Table 1 lists exemplary alpha-4/beta-1 integrin inhibitory compounds that were found to have activity in the foregoing assays. Moreover, experiments in support of the present invention revealed that all 373 compounds described in parent applications U.S. patent application Ser. No. 08/904, 424, filed Jul. 31, 1997, and U.S. Provisional Application No. 60/054,453, filed Aug. 1, 1997, and/or in co-owned application PCT/US98/15324 filed concurrently herewith, all of which are incorporated herein by reference, exhibited sufficient alpha-4/beta-1 integrin inhibitory activity to be considered candidates for alpha-9 screening, as described in Part B, below.

TABLE 1

| Compound | Name |
| --- | --- |
| 1 | N-(toluene-4-sulfonyl)-L-prolyl-L-4(4-methylpiperazin-1-ylcarbonyloxy)phenylalanine |
| 2 | N-(toluene-4-sulfonyl)-L-prolyl-L-4(N,N-dimethylcarbamyloxy)phenylalanine |
| 3 | N-(1-methylpyrazole-4-sulfonyl)-L-prolyl-L-4-(N,N-dimethylcarbamyloxy)phenylalanine |
| 4 | N-(toluene-4-sulfonyl)-L-(1,1-dioxo-5,5-dimethyl)thiaprolyl-L-4-(N,N-dimethylcarbamyloxy)phenylalanine |
| 5 | N-(toluene-4-sulfonyl)-N-methyl-L-alaninyl-L-4-(N,N-dimethylcarbamyloxy)phenylalanine |
| 6 | N-(toluene-4-sulfonyl)-L-[1,1-dioxo)thiamorpholin-3-carbonyl]-L-4-(N,N-dimethylcarbamyloxy)phenylalanine |
| 7 | N-(N-p-toluenesulfonyl)prolyl-4-(piperazinoyloxy)phenylalanine |
| 8 | N-(N-p-toluenesulfonyl)sarcosyl-4-(N,N-dimethylcarbamyloxy)phenylalanine |
| 9 | N-(toluene-4-sulfonyl)-L-(5,5-dimethyl)thiaprolyl-L-4-[3-(N,N-dimethyl)propoxy]phenylalanine |

It is understood that alpha-4/beta-1 integrin modulatory activity may alternatively be measured in one or more of other appropriate assays known and available to those skilled in the art. While absolute inhibitory concentration values may vary from assay to assay and operator to operator, compounds that inhibit (or enhance) activity at a concentration no higher than about 1 mM, and preferably no higher than about 100 μM should be considered as candidates for alpha-9 integrin modulatory agents.

B. Alpha-9 Integrin Binding and Activity Assays

Example 2 describes exemplary assays for measuring alpha-9 integrin binding and activity. A convenient assay is one similar to the one described above, with reference to binding of alpha-4-beta-1 integrin to VCAM-1, using the same 15/7 antibody that recognizes activated beta-1 subunit, but substituting into the assay cells expressing the alpha-9 subunit. In experiments carried out in support of the present invention, SW480 cells were transfected with a plasmid containing an expressable coding region for the alpha-9 subunit, as described by Yokosaki, et al. (1994, 1996), both of which references are incorporated herein by reference. Compounds were assessed for ability to interfere with binding of these cells to tenascin.

Compounds 1–9 described herein potently induced the ligand-occupied epitope (15/7) on the $\alpha_9$ transfected cells, but not in control mock-transfected cells, at concentrations less than about 1 μM. Furthermore, activity of these compounds in a binding saturation assay was found to correspond to their abilities to inhibit $\alpha_9$-dependent cell adhesion to tenascin according to the methods set forth in Example 2. Based on these experiments, alpha-9 inhibitory activity can be defined as inhibition of alpha-9 integrin binding to tenascin, as evidenced by an $IC_{50}$ or effective concentration of less than about 100 μM, and preferably less than about 20 μM.

More generally, it is appreciated that active alpha-9 integrin antagonist compounds useful in the pharmaceutical compositions and methods of the invention will have activities that are defined relative to the potencies exemplified by the nine compounds described above. That is, in accordance with a preferred embodiment of the present invention, active alpha-9 antagonist compounds have activities reflecting at least 1/1000 and preferably at least 1/100 the potency of the lowest activity compound exemplified herein. Thus, a practitioner engaged in screening compounds will know to test the above-listed compounds as reference standards and to compare the activities of test compounds to the activities of the reference standards described above. According to this preferred embodiment of the invention, a test compound will be considered active if it exhibits an activity that is at least 1/1000, and preferably at least 1/100 that of the lowest activity compound exemplified above. By way of illustration, if the lowest activity reference standard compound in a given assay were to exhibit an $IC_{50}$ of 1 μM, test compounds exhibiting $IC_{50}$s as high as 1000 μM (1 mM) and preferably 100 μM would be considered to be active alpha-9 antagonists in accordance with the present invention.

Methods for preparing the above-referenced reference standard compounds are found, for example in Example 4 herein (compounds 1–6), in parent application U.S. patent application Ser. No. 08/904,424, filed Jul. 31, 1997, or U.S. Provisional Application No. 60/054,453, filed Aug. 1, 1997 (both of which are concurrently filed with the present application as PCT/US98/15324), or in U.S. patent application Ser. No. 08/920,394, filed Jul. 31, 1997, filed concurrently as PCT/US98/15313, all of which are incorporated herein by reference.

C. Selectivity for Alpha-9 Integrin

A further desirable activity of alpha-9 modulatory compounds in accordance with the present invention is an ability to selectively regulate alpha-9 integrin activity. In experiments carried out in support of the present invention, compounds were tested for activity in assays measuring activity of various integrins, including $\alpha 4\beta_7$ integrin as assessed by binding to MadCAM1, $\alpha_5\beta_1$ integrin as assessed by binding to fibronectin, $\alpha L\beta_2$ integrin, as assessed by binding to ICAM-1, using methods and reagents well known in the art. As discussed above, the foregoing compounds were also tested for alpha-4/beta-1 integrin binding to VCAM-1.

While many of the alpha-4/beta-1 integrin antagonists tested exhibited equivalent activities in the alpha-4/beta-1 integrin and alpha-9 integrin activity assays described herein, compounds were also found which 10-fold or greater selectivity for inhibition in one of the assays, as compared to the other.

All nine reference compounds described herein tested exhibited at least a 100-fold selectivity in the alpha-9 integrin assay, compared to the $\alpha_5\beta_1$ integrin and $\alpha_4\beta_7$ integrin assays and were inactive in the $\alpha L\beta_2$ integrin assay. Thus, these compounds are characterized as selective for alpha-9 integrin activity, as opposed to $\alpha_5\beta_1$, $\alpha_4\beta$ or $\alpha L\beta_2$ activity. Such selectivity may be desirable when specificity of activity is particularly desirable. Guided by the teachings of the present specification and the particular therapeutic application for which a particular test compound is to be used, practitioners skilled in the art will be able to (a) determine appropriate drug activity assays for purposes of comparison, and (b) select a selectivity ratio that is acceptable in the context of such therapeutic application.

D. Criteria for Selection of Alpha-9 Integrin Modulatory Compounds

Active alpha-9 integrin modulatory compounds in accordance with the present invention increase or decrease binding between alpha-9 integrin and one or more of its ligands, for example tenascin, osteopontin or VCAM-1, at a concentration that is of sufficient potency to provide a pharmaceutical composition. Generally, it is appreciated that useful drugs will be active in vitro or in vivo at concentrations less than about 100 μM and preferably less than about 20 μM. Therefore, in accordance with the present invention, useful alpha-9 integrin modulatory compounds will be active in this concentration range in an appropriate alpha-9 integrin activity, as described herein.

Exemplified herein are a number of active alpha-9 integrin antagonist or inhibitory compounds all of which have the requisite potency to be active. In accordance with the present invention, it is suggested that these compounds can be used as reference standards in the exemplified alpha-9 antagonist activity assay or in any other appropriate alpha-9 activity assay. A compound that is run in the same assay will be considered active if it exhibits an activity that is at least $\frac{1}{1000}$, and preferably at least $\frac{1}{100}$ the potency of the lowest activity reference compound selected from compounds 1–9 illustrated herein.

According to a particularly useful embodiment of the present invention exemplified herein, it is appreciated that compounds having alpha-4/beta-1 modulatory activity form a particularly useful "library" of starting compounds for identifying alpha-9 modulatory compounds. This is a useful, but not essential criterion for selecting compounds for use in the pharmaceutical compositions and methods of the present invention.

Additionally, it is appreciated that it may be advantageous to select alpha-9 modulatory compounds that are relatively selective for modulating alpha-9 integrin activity, as compared to other integrins or other pharmacological activities. Suggested criteria for selectivity are provided above.

It is further appreciated that compounds useful in the pharmaceutical compositions and treatment methods described herein should conform to acceptable levels of toxicity; persons skilled in the art will further subject test candidate compounds in toxicity assays according to standard methods known in the art and/or mandated by the appropriate regulatory authority.

V. Utility

Alpha-9 integrin modulatory compounds selected in accordance with the present activity have utility in pharmaceutical compositions, methods of treatments. In addition, the selection assays described above are useful in identifying compounds for use in such compositions and methods.

A. Pharmaceutical Compositions and Treatment of Disorders Associated with Alpha-9 Integrin Binding Alpha-9 integrin modulatory compounds identified and selected in accordance with the present invention find use in a number of disorders associated with alpha-9 integrin activity. Particularly, in view of discoveries described herein with respect to the neutrophil localization of alpha-9 integrin, as well as its ability to interact with VCAM-1, it is appreciated that alpha-9 integrin inhibitory compounds will find particular utility in the treatment of a variety of disorders which include an inflammatory component, particularly those to which the inflammatory component is associated with VCAM-1 binding to alpha-9 integrin.

1. Therapeutic Indications

The pharmaceutical compositions of the present invention can be used to block or inhibit cellular adhesion associated with a number of diseases and disorders. For instance, a number of inflammatory disorders are associated with integrins or neutrophils. Treatable disorders include, e.g., transplantation rejection (e.g., allograft rejection), Alzheimer's disease, atherosclerosis, AIDS dementia, diabetes (including acute juvenile onset diabetes), retinitis, cancer metastases, rheumatoid arthritis, various lung disorders including asthma, nephritis, and acute and chronic inflammation, including atopic dermatitis, psoriasis, myocardial ischemia, and inflammatory bowel disease (including Crohn's disease and ulcerative colitis). In preferred embodiments, the pharmaceutical compositions are used to treat inflammatory brain disorders, such as Alzheimer's disease, AIDS dementia, multiple sclerosis (MS), viral meningitis and encephalitis, as well as stroke (cerebral ischemia) related disorders.

More particularly, since alpha-9 integrin binding is predictive of in vivo utility for inflammatory conditions mediated by alpha-9 integrin, compositions and methods of the invention can be used for treating, by way of example, airway hyper-responsiveness and occlusion that occurs with chronic asthma, smooth muscle cell proliferation in atherosclerosis, vascular occlusion following angioplasty, fibrosis and glomerular scarring as a result of renal disease, aortic stenosis, hypertrophy of synovial membranes in rheumatoid arthritis, and inflammation and scarring that occur with the progression of ulcerative colitis and Crohn's disease In accordance with the present invention, it is appreciated that alpha-9 integrin modulatory compounds, particularly those exhibiting inhibitory activity, will find utility in treating the many, if not all, of the foregoing disorders. Compounds selected for inhibitory activity in accordance with the methods described herein are then tested in appropriate animal models, for example, to determine dosage, volumes of distribution and the like. Efficacy may also be confirmed in such models, which are well known in the art.

For example, appropriate in vivo models for demonstrating efficacy in treating inflammatory responses include an asthma model in mice, rats, guinea pigs, goats or primates, as well as other inflammatory models in which alpha-9 integrins are implicated.

Asthma is a disease characterized by increased responsiveness of the tracheobronchial tree to various stimuli potentiating paroxysmal constriction of the bronchial airways. The stimuli cause release of various mediators of inflammation from IgE-coated mast cells including histamine, eosinophilic and neutrophilic chemotactic factors, leukotrines, prostaglandin and platelet activating factor. Release of these factors recruits basophils, eosinophils and neutrophils, which cause inflammatory injury. In accordance with the present invention, it is believed that airway hyper-responsiveness and occlusion that occur with chronic asthma are mediated, at least in part, by alpha-9 integrin binding interactions. This is verified in a standard model such as described in Example 3, herein.

Inflammatory bowel disease is a collective term for two similar diseases referred to as Crohn's disease and ulcerative colitis. Crohn's disease is an idiopathic, chronic ulceroconstrictive inflammatory disease characterized by sharply delimited and typically transmural involvement of all layers of the bowel wall by a granulomatous inflammatory reaction. Any segment of the gastrointestinal tract, from the mouth to the anus, may be involved, although the disease most commonly affects the terminal ileum and/or colon. Ulcerative colitis is an inflammatory response limited largely to the colonic mucosa and submucosa. Lymphocytes and macrophages are numerous in lesions of inflammatory bowel disease and may contribute to inflammatory injury Atherosclerosis is a disease of arteries (e.g., coronary, carotid, aorta and iliac). The basic lesion, the atheroma, consists of a raised focal plaque within the intima, having a core of lipid and a covering fibrous cap. Atheromas compromise arterial blood flow and weaken affected arteries. Myocardial and cerebral infarcts are a major consequence of this disease. Macrophages and leukocytes are recruited to atheromas and contribute to inflammatory injury.

Rheumatoid arthritis is a chronic, relapsing inflammatory disease that primarily causes impairment and destruction of joints. Rheumatoid arthritis usually first affects the small joints of the hands and feet but then may involve the wrists, elbows, ankles and knees. The arthritis results from interaction of synovial cells with leukocytes that infiltrate from the circulation into the synovial lining of the joints. See e.g., Paul, Immunology (3d ed., Raven Press, 1993).

Another indication for the compounds of this invention is in treatment of organ or graft rejection mediated by VLA-4. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue. CD8+ cells, CD4 cells and monocytes are all involved in the rejection of transplant tissues. Compounds of this invention which bind to alpha-9 integrin are useful, inter alia, to block alloantigen-induced immune responses in the donee thereby preventing such cells from participating in the destruction of the transplanted tissue or organ. See, e.g., Paul et al., Transplant International 9, 420–425 (1996); Georczynski et al., Immunology 87, 573–580 (1996); Georcyznski et al., Transplant. Immunol. 3, 55–61 (1995); Yang et al., Transplantation 60, 71–76 (1995); Anderson et al., APMIS 102, 23–27 (1994).

A related use for compounds of this invention which bind to alpha-9 integrin is in modulating the immune response involved in "graft versus host" disease (GVHD). See e.g., Schlegel et al., J. Immunol. 155, 3856–3865 (1995). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The therapeutic agents of the present invention are used, inter alia, to block activation of the donor T-cells thereby interfering with their ability to lyse target cells in the host.

A further use of the compounds of this invention is inhibiting tumor metastasis. Several tumor cells have been reported to express integrins, such as VLA-4 and block adhesion of such cells to endothelial cells. Steinback et al., Urol. Res. 23, 175–83 (1995); Orosz et al., Int. J. Cancer 60, 867–71 (1995); Freedman et al., Leuk. Lymphoma 13, 47–52 (1994); Okahara et al., Cancer Res. 54, 3233–6 (1994).

A further use of the compounds of this invention is in treating multiple sclerosis. Multiple sclerosis is a progressive neurological autoimmune disease that affects an estimated 250,000 to 350,000 people in the United States. Multiple sclerosis is thought to be the result of a specific autoimmune reaction in which certain leukocytes attack and initiate the destruction of myelin, the insulating sheath covering nerve fibers. In an animal model for multiple sclerosis, murine monoclonal antibodies directed against integrins such as VLA-4 have been shown to block the adhesion of leukocytes to the endothelium, and thus prevent inflammation of the central nervous system and subsequent paralysis in the animals.

2. Pharmaceutical Compositions

Pharmaceutical compositions of the invention are suitable for use in a variety of drug delivery systems. Suitable formulations for use in the present invention are found in Remington's Pharmaceutical Sciences, Mace Publishing Company, Philadelphia, Pa., 17th ed. (1985). Such pharmaceutical compositions are particularly useful in treating diseases having an inflammatory component, such as those discussed in Part 1, above.

Pharmaceutical compositions of the present invention can also be used in in vivo diagnostic imaging to identify, e.g., sites of inflammation, radioisotopes are typically used in accordance with well known techniques. The radioisotopes may be bound to the peptide either directly or indirectly using intermediate functional groups. For instance, chelating agents such as diethylenetriaminepentacetic acid (DTPA) and ethylenediaminetetraacetic acid (EDTA) and similar molecules have been used to bind proteins to metallic ion radioisotopes. The complexes can also be labeled with a paramagnetic isotope for purposes of in vivo diagnosis, as in magnetic resonance imaging (MRI) or electron spin resonance (ESR), both of which are well known. In general, any conventional method for visualizing diagnostic images can be used. Usually gamma- and positron-emitting radioisotopes are used for camera imaging and paramagnetic isotopes are used for MRI. Thus, the compounds can be used to monitor the course of amelioration of an inflammatory response in an individual. By measuring the increase or decrease in macrophages and/or neutrophils expressing alpha-9 integrin it is possible to determine whether a particular therapeutic regimen aimed at ameliorating the disease is effective.

Compounds having the desired biological activity may be modified as necessary to provide desired properties such as improved pharmacological properties (e.g., in vivo stability, bio-availability), or the ability to be detected in diagnostic applications. For instance, inclusion of one or more D-amino acids in the sulfonamide compositions described herein typically increases in vivo stability. Stability can be assayed in a variety of ways such as by measuring the half-life of the proteins during incubation with peptidases or human plasma or serum. A number of such protein stability assays have been described (see, e.g., Verhoef, et al., Eur. J. Drug Metab. Pharmacokinet., 1990, 15(2):83–93).

In order to enhance serum half-life, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

Appropriate treatment dosages and dosage schedules are determined in accordance with the condition being treated, and a number of variables, including, but not limited to the intended mode of administration, the pharmacokinetics of the active compound, the size of the subject. For example, for intravenous administration, the dose will typically be in the range of about 20 $\mu$g to about 500 $\mu$g per kilogram body weight, preferably about 100 $\mu$g to about 300 $\mu$g per kilogram body weight. Suitable dosage ranges for intranasal administration are generally about 0.1 pg to 1 mg per kilogram body weight. Dosages can be based on appropriate estimates or can be determined empirically by persons skilled in the art. Generally, relative dosages can be estimated based on comparisons of potencies in one or more of the screening assays described herein.

Effective doses can be extrapolated from dose-response curves derived from in vitro or animal model test systems. In general, effective dosages can be estimated from the predictive in vitro assays described herein. That is, an effective dose is calculated to produce at the target tissue(s) in the body, a concentration of compound that is in the range of $\frac{1}{10}$ to 10-times the concentration of compound $IC_{50}$ in such an assay.

The compositions administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending clinician depending upon factors such as the severity of the inflammation, the age, weight and general condition of the patient, and the like.

B. Drug Screening Assays

The screening assays described herein are useful in identifying new compounds for use in the treatment methods and pharmaceutical compositions described above. At its most basic, the screening assay includes testing a candidate compound for its ability to interfere with (or enhance) binding between alpha-9 integrin and one or more of its ligands, such as osteopontin, VCAM-1 or tenascin. The test compounds can also be tested for the ability to competitively inhibit such binding, or between alpha-9 integrin and a labeled compound known to bind alpha-9 integrin such one of the compounds described herein or antibodies to alpha-9 integrin.

Preferably, the screening assay is used to identify alpha-9 integrin inhibitory compounds, since such compounds are, in accordance with the invention, particularly useful in treating inflammation in a variety of conditions, as discussed above. According to this aspect of the invention, a test compound is added to an assay system configured to detect binding between alpha-9 integrin and one or more of its ligands, such as osteopontin, VCAM-1 or tenascin, and compounds are tested for ability to inhibit such binding. Particularly useful compounds are those which exhibit activity which is in the range of, or at most about 100-times less potent than, the activity ranges defined by the reference standards provided herein (see Table 1).

As mentioned above, test compounds can be selected from a variety of sources, including combinatorial libraries, fermentation broths and the like. A particularly good source, identified herein, is the pool of compounds that are known to inhibit or are found to inhibit binding between alpha-4/beta-1 integrin (VLA-4) and one or more of its ligands, such as VCAM-1.

A number of formats can be used for assays for screening for drugs. In a preferred embodiment, assays will be adapted for high throughput screening. For example, alpha-9 integrin or membranes from cells expressing alpha-9 integrin can be immobilized on a solid surface, such as a microtiter plate or glass fiber filter optionally adapted with binding aids such as antibodies to a non-ligand binding portion of the molecule. Such assay formats generally employ at least one detectably-labeled assay components. The labeling systems can be in a variety of forms. The label may be coupled directly or indirectly to the desired component of the assay according to methods well known in the art. A wide variety of labels may be used. The component may be labeled by any one of several methods. The most common method of detection is the use of autoradiography with $^{3}H$, $^{125}I$, $^{35}S$, $^{14}C$, or $^{32}P$ labeled compounds and the like. Non-radioactive labels include ligands which bind to labeled antibodies, fluorophores, chemiluminescent agents, enzymes and antibodies which can serve as specific binding pair members for a labelled ligand. The choice of label depends on sensitivity required, ease of conjugation with the compound, stability requirements, and available instrumentation.

In vitro uses of pharmaceutical compositions of the invention include diagnostic applications such as monitoring inflammatory responses by detecting the presence of macrophages, including neutrophils, expressing alpha-9 integrin. Compositions of this invention can also be used for isolating or labeling such cells.

For assays to measure the ability to block adhesion to brain endothelial cells, the assays described in International Patent Application Publication No. WO 91/05038 are particularly preferred, as adapted to the reagents described herein, according to methods well within the skill of the practitioner. This application is incorporated herein by reference in its entirety.

The following examples illustrate, but in no way are intended to limit the present invention.

EXAMPLES

Example 1

Binding of Compounds to $\alpha_4\beta_1$ Integrin (VLA-4)

A. 15/7 Antibody Assay

The cell adhesion assay described below is based on an assay detailed in a publication by Yednock, et al. (1995), which is incorporated herein by reference. An in vitro assay was used to assess binding of candidate compounds to $\alpha_4\beta_1$ integrin. Compounds which bind in this assay can be used to assess VCAM-1 levels in biological samples by conventional assays (e.g., competitive binding assays). This assay is sensitive to $IC_{50}$ values as low as about 1 nM.

The activity of $\alpha 4\beta 1$ integrin was measured by the interaction of soluble VCAM-1 with Jurkat cells (e.g., American Type Culture Collection Nos. TIB 152, TIB 153, and CRL 8163; American Type Culture Collection, Manassas, Va.), a human T-cell line which expresses high levels of $\alpha 4\beta 1$ integrin. VCAM-1 interacts with the cell surface in an $\alpha 4\beta 1$ integrin-dependent fashion (Yednock).

Recombinant soluble VCAM-1 was expressed as a chimeric fusion protein containing the seven extracellular domains of VCAM-1 on the N-terminus and the human IgG1 heavy chain constant region on the C-terminus. The VCAM-1 fusion protein was made and purified by the manner described by Yednock, supra. Jurkat cells were grown in RPMI 1640 supplemented with 10% fetal bovine serum, penicillin, streptomycin and glutamine as described by Yednock, supra. Jurkat cells were incubated with 1.5 mM MnCl2 and 5 µg/mL 15/7 antibody for 30 minutes on ice. Mn+2 activates the receptor to enhance ligand binding, and 15/7 is a monoclonal antibody that recognizes an activated/ligand occupied conformation of $\alpha_4\beta_1$ integrin and locks the molecule into this conformation thereby stabilizing the VCAM-1/$\alpha_4\beta_1$ integrin interaction. Yednock, et al., supra. Antibodies similar to the 15/7 antibody have been prepared by other investigators (Luque, et al, 1996, J. Bio. Chem. 271:11067) and may be used in this assay.

Cells were then incubated for 30 minutes at room temperature with candidate compounds, in various concentrations ranging from 66 µg/mL to 0.01 µg/mL using a standard 5-point serial dilution. 15 µL soluble recombinant VCAM-1 fusion protein was then added to Jurkat cells and incubated for 30 minutes on ice. (Yednock et al., supra.). Cells were then washed two times and resuspended in PE-conjugated goat F(ab')2 anti-mouse IgG Fc (Immunotech, Westbrook, Me.) at 1:200 and incubated on ice, in the dark, for 30 minutes. Cells were washed twice and analyzed with a standard fluorescence activated cell sorter ("FACS") analysis as described in Yednock, et al., supra.

When tested in this assay, each of the compounds as described in Examples 1–373 of parent application U.S. Ser. No. 08/904,424 (PCT/US98/15324) or the corresponding carboxylic acids of the ester compounds, i.e., the prodrugs) exhibit $IC_{50}$s of 15 µM or less.

B. In Vitro Saturation Assay for Determining Binding of Candidate Compounds to $\alpha_4\beta_1$ Log-growth Jurkat cells were washed and resuspended in normal animal plasma containing 20 µg/ml of the 15/7 antibody (described in the above example). The Jurkat cells were diluted two-fold into either normal plasma samples containing known candidate compound amounts in various concentrations ranging from 66 µg/mL to 0.01 µg/mL, using a standard 12 point serial dilution for a standard curve, or into plasma samples obtained from the peripheral blood of candidate compound-treated animals. Cells were then incubated for 30 minutes at room temperature, washed twice with phosphate-buffered saline ("PBS") containing 2% fetal bovine serum and 1 mM each of calcium chloride and magnesium chloride (assay medium) to remove unbound 15/7 antibody. The cells were then exposed to phycoerythrin-conjugated goat F(ab')2 anti-mouse IgG Fc (Immunotech, Westbrook, Me.), which has been adsorbed for any non-specific cross-reactivity by co-incubation with 5% serum from the animal species being studied, at 1:200 and incubated in the dark at 4?C for 30 minutes. Cells were washed twice with assay medium and resuspended in the same. They are then analyzed with a standard fluorescence activated cell sorter ("FACS") analysis as described in Yednock et al. J. Bio. Chem., 1995, 270:28740.

The data were graphed as fluorescence versus dose, e.g., in a normal dose-response fashion. The dose levels that result in the upper plateau of the curve represent the levels needed to obtain efficacy in an in vivo model.

This assay may also be used to determine the plasma levels needed to saturate the binding sites of other integrins, such as the $\alpha 9\beta_1$ integrin, using appropriate cells expressing alpha-9 integrin, as described in Example 2, below.

Example 2

Cell Adhesion to Tenascin

The following assay was first described by Yokosaki, et al. (1994) and can be used to estimate serum levels of compounds required for treating inflammatory diseases related to alpha-9 integrin binding, as exemplified by the asthma model detailed in Example 3, below.

Evaluation of cell attachment to extracellular matrix proteins was performed as follows: Briefly, wells of non-tissue culture-treated polystyrene 96-well flat-bottom microtiter plates (Linbro/Titertek, Flow Laboratories, McLean, Va.) were coated by incubation with intact tenascin (10 µg/ml) or recombinant tenascin fragments (1 µg/ml to 10 µg/ml) in PBS at 37° C. for 1 h or at 4° C. for 16 h. Wells were washed with PBS and then blocked with 1% bovine serum albumin in DMEM. 50,000 cells (SW480 cell line transfected with alpha-9 integrin, (Yokosaki, 1996) a gift of D. Sheppard, Dept. of Medicine, University of California, San Francisco) were added to each well in 200 µl of serum-free DMEM containing 0.05% bovine serum albumin. For blocking experiments, cells were incubated with the relevant reagent for 30 min at 4° C. before plating. Plates were centrifugated at 10×g for 5 min and then incubated for 1 h at 37° C. in a humidified atmosphere with 5% $CO_2$. Nonadherent cells were removed by centrifugation top-side-down at 48×g for 5 min. The attached cells were fixed with 1% formaldehyde and stained with 0.5 crystal violet, and excess dye was washed off with PBS. The cells were solubilized in 50 µl of 2% Triton X-100 and quantified by measuring the absorbance at 595 nm in a Microplate Reader (Bio-Rad). Positive adhesion results in this assay correlate with increased absorbance.

Isolated populations of neutrophils can also be used in the foregoing assay in place of the transfected cells. In addition, ligands such as fibronectin, VCAM-1 or osteopontin can be substituted in this assay.

Example 3

Asthma Model

Inflammatory conditions mediated by alpha-9 integrin include, for example, airway hyper-responsiveness and occlusion that occurs with chronic asthma. The following describes an asthma model which can be used to study the in vivo effects of the compounds of this invention for use in treating asthma.

Following the procedures described by Abraham et al, J. Clin. Invest, 93:776–787 (1994) and Abraham et al, Am J. Respir Crit Care Med, 156:696–703 (1997), both of which are incorporated by reference in their entirety, compounds of this invention are formulated into an aerosol and administered to sheep which are hypersensitive to Ascaris suum antigen. Compounds which decrease the early antigen-induced bronchial response and/or block the late-phase airway response, e.g., have a protective effect against antigen-induced late responses and airway hyper-responsiveness ("AHR"), are considered to be active in this model. Allergic sheep which are shown to develop both early and late bronchial responses to inhaled Ascaris suum antigen are used to study the airway effects of the candidate compounds. Following topical anesthesia of the nasal passages with 2% lidocaine, a balloon catheter is advanced through one nostril into the lower esophagus. The animals are then intubated with a cuffed endotracheal tube through the other nostril with a flexible fiberoptic bronchoscope as a guide. Pleural pressure is estimated according to Abraham (1994). Aerosols (see formulation below) are generated using a disposable medical nebulizer that provides an aerosol with a mass median aerodynamic diameter of 3.2 µm as determined with an Andersen cascade impactor. The nebulizer is connected to a dosimeter system consisting of a solenoid valve and a source of compressed air (20 psi). The output of the nebulizer is directed into a plastic T-piece, one end of which was connected to the inspiratory port of a piston respirator. The solenoid valve is activated for 1 second at the beginning of the inspiratory cycle of the respirator. Aerosols are delivered at VT of 500 mL and a rate of 20 breaths/minute. A 0.5% sodium bicarbonate solution only was used as a control.

To assess bronchial responsiveness, cumulative concentration-response curves to carbachol are generated according to Abraham (1994). Bronchial biopsies are taken prior to and following the initiation of treatment and 24 hours after antigen challenge. Bronchial biopsies are performed according to Abraham (1994). An in vitro adhesion study of alveolar macrophages is also performed according to Abraham (1994), and a percentage of adherent cells is calculated.

Aerosol Formulation

A solution of the candidate compound in 0.5% sodium bicarbonate/saline (w/v) at a concentration of 30.0 mg/mL is prepared using the following procedure:

A. Preparation of 100 mL of 0.5% Sodium Bicarbonate/Saline Stock Solution:

1. Add 0.5 g sodium bicarbonate into a 100 mL volumetric flask.
2. Add approximately 90.0 mL saline and sonicate until dissolved.
3. Q.S. to 100.0 mL with saline and mix thoroughly.

B. Preparation of 10.0 mL of 30.0 mg/mL Candidate Compound:

1. Add 0.300 g of the candidate compound into a 10.0 mL volumetric flask.
2. Add approximately 9.7 mL of 0.5% sodium bicarbonate/saline stock solution.
3. Sonicate until the candidate compound is completely dissolved.
4. Q.S. to 10.0 mL with 0.5% sodium bicarbonate/saline stock solution and mix thoroughly.

Example 4

Synthesis of alpha-9 Integrin-modulatory Compounds

This Example provides representative organic syntheses of precursors and reference standard compounds described herein. Parent applications U.S. patent application Ser. No. 08/904,424, filed Jul. 31, 1997, and U.S. Provisional Application No. 60/054,453, filed Aug. 1, 1997, as well as co-owned, concurrently filed U.S. patent application Ser. No. 09/126,958 and corresponding PCT application PCT/US98/15324 all of which applications are incorporated herein by reference in their entireties, are referenced specifically for their methods of preparation of these and many other related compounds.

A. General Reference Methods

Method 1: N-Tosylation Procedure

N-Tosylation of the appropriate amino acid was conducted via the method of Cupps, Boutin and Rapoport J. Org. Chem. 1985, 50, 3972.

Method 2: Methyl Ester Preparation Procedure

Amino acid methyl esters were prepared using the method of Brenner and Huber Helv. Chim. Acta 1953, 36, 1109.

Method 3: BOP Coupling Procedure

The desired dipeptide ester was prepared by the reaction of a suitable N-protected amino acid (1 equivalent) with the appropriate amino acid ester or amino acid ester hydrochloride (1 equivalent), benzotriazol-1-yloxy-tris(dimethylamino)phosphonium hexafluorophosphate [BOP] (2.0 equivalent), triethylamine (1.1 equivalent), and DMF. The reaction mixture was stirred at room temperature overnight. The crude product is purified flash chromatography to afford the dipeptide ester.

Method 4: Hydrogenation Procedure I

Hydrogenation was performed using 10% palladium on carbon (10% by weight) in methanol at 30 psi overnight. The mixture was filtered through a pad of Celite and the filtrate concentrated to yield the desired amino compound.

Method 5: Hydrolysis Procedure I

To a chilled (0?C) THF/H2O solution (2:1, 5–10 mL) of the appropriate ester was added LiOH (or NaOH) (0.95 equivalents). The temperature was maintained at 0° C. and the reaction was complete in 1–3 hours. The reaction mixture was extracted with ethyl acetate and the aqueous phase was lyophilized resulting in the desired carboxylate salt.

Method 6: Ester Hydrolysis Procedure II

To a chilled (0° C.) THF/H2O solution (2:1, 5–10 mL) of the appropriate ester was added LiOH (1.1 equivalents). The temperature was maintained at 0° C. and the reaction was complete in 1–3 hours. The reaction mixture was concentrated and the residue was taken up into H2O and the pH adjusted to 2–3 with aqueous HCl. The product was extracted with ethyl acetate and the combined organic phase was washed with brine, dried over MgSO4, filtered and concentrated to yield the desired acid.

Method 7: Ester Hydrolysis Procedure III

The appropriate ester was dissolved in dioxane/H2O (1:1) and 0.9 equivalents of 0.5 N NaOH was added. The reaction was stirred for 3–16 hours and than concentrated. The resulting residue was dissolved in H2O and extracted with ethyl acetate. The aqueous phase was lyophilized to yield the desired carboxylate sodium salt.

Method 8: Sulfonylation Procedure I

To the appropriately protected aminophenylalanine analog (11.2 mmol), dissolved in methylene chloride (25 ml) and cooled to −78?C was added the desired sulfonyl chloride (12 mmol) followed by dropwise addition of pyridine (2 mL). The solution was allowed to warm to room temperature and was stirred for 48 hr. The reaction solution was transferred to a 250 mL separatory funnel with methylene chloride (100 mL) and extracted with 1N HCl (50 mL×3), brine (50 mL), and water (100 mL). The organic phase was dried (MgSO4) and the solvent concentrated to yield the desired product.

Method 9: Reductive Amination Procedure

Reductive amination of Tos-Pro-p-NH2-Phe with the appropriate aldehyde was conducted using acetic acid, sodium triacetoxyborohydride, methylene chloride and the combined mixture was stirred at room temperature overnight. The crude product was purified by flash chromatography.

Method 10: BOC Removal Procedure

Anhydrous hydrochloride (HCl) gas was bubbled through a methanolic solution of the appropriate Boc-amino acid ester at 0?C for 15 minutes and the reaction mixture was stirred for three hours. The solution was concentrated to a syrup and dissolved in Et2O and reconcentrated. This procedure was repeated and the resulting solid was placed under high vacuum overnight.

Method 11: Tert-butyl Ester Hydrolysis Procedure I

The tert-butyl ester was dissolved in CH2Cl2 and treated with TFA. The reaction was complete in 1–3 hr at which time the reaction mixture was concentrated and the residue dissolved in H2O and lyophilized to yield the desired acid.

B. Preparations

Prep 1 Synthesis of N-(Toluene-4-sulfonyl)-L-prolyl-L-4-(4-methylpiperazin-1-ylcarbonyloxy) phenylalanine Ethyl Ester The title compound was prepared following the procedure outlined for the preparation of Prep 4 and substitution of appropriate starting materials.

NMR data were as follows: 1H NMR (CD3)2SO): δ=8.33 (d, 1H), 7.70 (d, 2H), 7.41 (d, 2H), 7.24 (d, 2H), 7.00 (d, 2H), 4.52–4.44 (m, 1H), 4.09–4.00 (m, 3H), 3.53 (bs, 2H), 3.38–3.31 (m, 3H), 3.11–3.01 (m, 3H), 2.39 (s, 3H), 2.32 (bs, 4H), 2.19 (s, 3H), 1.61–1.50 (m, 3H), 1.43–1.38 (m, 1H), 1.13 (t, 3H). 13C NMR (CD3)2SO): δ=171.1, 171.1, 153.9, 149.8, 143.6, 134.1, 133.9, 130.0, 129.8, 127.4, 121.5, 61.2, 60.7, 54.2, 54.1, 53.3, 49.0, 45.7, 44.0, 43.4, 35.8, 30.5, 23.8, 21.0, 14.0.

Prep 2 Synthesis of N-(Toluene-4-sulfonyl)-L-prolyl-L-4-(N,N-dimethylcarbamyloxy) phenylalanine Ethyl Ester (Compound 2)

Into a reaction vial were combined 7.00 g (15.2 mmol, 1.0 eq) Ts-Pro-Tyr(H)-OEt and 1.86 g (15.2 mmol, 1.0 eq) DMAP. Methylene chloride (50 mL), triethylamine (2.12 mL—1.54 g, 15.2 mmol, 1.0 eq), and dimethylcarbamyl chloride (1.68 mL—1.96 g, 18.2 mmol, 1.2 eq) were then added. The vial was capped tightly, and the reaction solution swirled to obtain a homogeneous solution. The reaction solution was then heated to 40° C. After 48 h, TLC of the resulting colorless solution indicated complete conversion. The workup of the reaction solution was as follows: add 50 mL EtOAc and 50 mL hexanes to the reaction mixture, and wash with 3×50 mL 0.5 mL hexanes to the reaction mixture, and wash with 3×50 mL 0.5 M citric acid, 2×50 mL water, 2×50 mL 10% K2CO3, and 1×50 mL sat. NaCl. Dry with MgSO4. Filter. Evaporate to obtain 8.00 g (99%) of the title compound as a clear oil, which solidifies upon standing. Recrystallize from 5:3:2 heptane/EtOAc/CH2Cl2.

NMR data were as follows: 1H NMR (CD3)2SO): δ=8.32 (d, 1H), 7.70 (d, 2H), 7.41 (d, 2H), 7.23 (d, 2H), 7.00 (d, 2H), 4.52–4.44 (m, 1H), 4.09–4.02 (m, 3H), 3.37–3.31 (m, 1H), 3.11–2.96 (m, 3H), 3.00 (s, 3H), 2.87 (s, 3H), 2.39 (s, 3H), 1.61–1.50 (m, 3H), 1.43–1.38 (m, 1H), 1.13 (t, 3H). 13C NMR (CD3)2SO): δ=171.1, 171.1, 154.0, 150.0, 143.6, 133.9, 133.9, 130.0, 129.8, 127.4, 121.5, 61.2, 60.6, 53.3, 49.0, 36.3, 36.1, 35.8, 30.5, 23.8, 21.0, 14.0.

Prep 3 Synthesis of N-(Toluene-4-sulfonyl)-L-prolyl-L-4-(4-methylpiperazin-1-ylcarbonyloxy) phenylalanine Isopropyl Ester The title compound was prepared following the procedure outlined for the preparation of Prep 4 and substitution of appropriate starting materials.

NMR data were as follows: 1H NMR (CDCl3): δ=7.72 (d, 2H), 7.36 (d, 1H), 7.33 (d, 2H), 7.16 (d, 2H), 7.03 (d, 2H), 5.07 (Sept., 1H), 4.78 (dt, 1H), 4.08–4.05 (m, 1H), 3.67 (bs, 2H), 3.57 (bs, 2H), 3.41–3.35 (m, 1H), 3.24 (dd, 1H), 3.15–3.07 (m, 1H), 3.04 (dd, 1H), 3.46–2.43 (m, 7H), 2.34 (s, 3H), 2.05–2.02 (m, 1H). 13C NMR (CDCl3): δ=170.9, 170.4, 153.6, 150.5, 144.3, 133.2, 133.1, 130.2, 130.0, 127.9, 121.7, 69.5, 62.2, 54.7, 53.4, 49.6, 46.1, 44.3, 43.7, 37.2, 29.7, 24.1, 21.6, 21.6, 21.4.

Prep 4 Synthesis of N-(Toluene-4-sulfonyl)-L-prolyl-L-4-(4-methylpiperazin-1-ylcarbonyloxy) phenylalanine tert-Butyl Ester Combine 41.2 g (84.34 mmol, 1.0 eq) Ts-Pro-Tyr(H)-OtBu and 17.0 g (84.34 mmol, 1.0 eq) 4-nitrophenyl chloroformate. Add 700 mL CH2Cl2. Cap with a septum. Attach a N2 line. Immerse the flask in a 4:1 water/EtOH+dry ice slurry, and stir to cool to −15° C. Add 29.38 mL (21.33 g, 210.81 mmol, 2.5 eq) Et3N over five minutes with stirring. Stir at −10 to −15° C. for 1 h. Add 9.35 mL (8.45 g, 84.34 mmol, 1.0 eq) N-methyl piperazine over 3 minutes with stirring. Stir overnight while warming to room temperature. Dilute with 700 mL hexanes. Wash repeatedly with 10% K2CO3, until no yellow color (4-nitrophenol) is seen in the aqueous layer. Wash with sat. NaCl. Dry over anhydrous MgSO4. Filter. Evaporate. Dissolve in 500 mL EtOH, and evaporate, to remove Et3N. Repeat once. Dissolve in 400 mL EtOH, and add 600 mL water with stirring, to precipitate a solid or oil. If an oil, stir vigorously to solidify. Isolate the solid by filtration. Repeat dissolution, precipitation, and filtration, once. Rinse with water to remove traces of yellow color. High vacuum to constant mass yields the title compound as a white solid.

NMR data were as follows: 1H NMR (CDCl3): δ=7.72 (d, 2H), 7.33 (d, 3H), 7.17 (d, 2H), 7.02 (d, 2H), 4.71 (q, 1H), 4.09–4.06 (m, 1H), 3.67 (bs, 2H), 3.57 (bs, 2H), 3.41–3.34 (m, 1H), 3.22 (dd, 1H), 3.16–3.09 (m, 1H), 3.03 (dd, 1H), 2.46–2.43 (m, 7H), 2.34 (s, 3H), 2.05–2.02 (m, 1H), 1.57–1.43 (m, 3H), 1.47 (s, 9H). 13C NMR (CDCl3): δ=171.8, 169.9, 153.6, 150.4, 144.3, 133.4, 133.1, 130.3, 130.0, 127.9, 121.6, 82.6, 62.3, 54.5, 53.8, 49.6, 46.1, 44.3, 43.7, 37.3, 29.7, 27.8, 24.1, 21.4.

Prep 5 Synthesis of N-(Toluene-4-sulfonyl)-L-prolyl-L-4-(4-methylpiperazin-1-ylcarbonyloxy) phenylalanine (Reference Compound 1)

The title compound was prepared from the product of Prep 1 using the procedure described in Method 7.

NMR data were as follows: 1H NMR (CD3OD): δ=7.74 (d, 2H), 7.42 (d, 2H), 7.26 (d, 2H), 7.04 (d, 2H), 4.58–4.54 (m, 1H), 4.16–4.12 (m, 1H), 3.70 (bs, 2H) 3.53 (bs, 2H), 3.43–3.31 (m, 1H), 3.26–3.13 (m, 7H), 2.82 (s, 3H), 2.43 (s, 3H), 1.98–1.94 (m, 1H), 1.76–1.51 (m, 3H). 13C NMR (CD3OD): δ=175.7, 173.6, 154.8, 151.6, 146.1, 136.3, 134.8, 131.9, 131.3, 129.1, 122.7, 63.6, 55.9, 53.9, 50.7, 43.5, 37.6, 31.3, 25.5, 21.5.

Prep 9 Synthesis of N-(Toluene-4-sulfonyl)-L-prolyl-L-4-(N,N-dimethylcarbamyloxy) phenylalanine The title compound was prepared from the product of Prep 2 using the procedure described in Method 7.

NMR data were as follows: 1H NMR (CD3)2SO: δ=8.13 (d, 1H), 7.70 (d, 2H), 7.41 (d, 2H), 7.23 (d, 2H), 6.99 (d, 2H), 4.51–4.44 (m, 1H), 4.11–4.09 (m, 1H), 3.40–3.34 (m, 2H), 3.11–2.94 (m, 3H), 3.00 (s, 3H), 2.87 (s, 3H), 2.39 (s, 3H), 1.59–1.36 (m, 4H). 13C NMR (CD3)2SO: δ=172.7, 171.2, 153.6, 150.2, 143.8, 134.3, 134.0, 130.2, 130.0, 127.6, 121.6, 61.3, 53.2, 49.0, 36.3, 36.1, 35.9, 30.4, 23.8, 21.0.

Prep 10 Synthesis of N-(Toluene-4-sulfonyl)-L-prolyl-L-3-(N,N-dimethylcarbamyloxy) phenylalanine Ethyl Ester The title compound was prepared following the procedure outlined for the preparation of Prep 2 and substitution of appropriate starting materials.

NMR data were as follows: 1H NMR (CDCl3): δ=7.74 (m, 2H), 7.70–7.36 (m, 4H), 7.24–7.14 (m, 3H), 6.93–4.90 (m, 1H), 4.78–4.27 (m, 3H), 4.05–3.55 (m, 0.5H), 3.48–3.43 (m, 0.5H), 3.37–3.30 (m, 3H), 3.02–3.08 (bs, 3H), 2.99 (bs, 3H), 2.45 (s, 1.5H), 2.43 (s, 1.5H), 2.12 (m, 1H), 198, 1.80 (m, 0.5M), 1.62–1.44 (m, 2.5H), 1.29 (t, 1.5H), 1.24 (t, 1.5H). 13C NMR (CDCl3): δ=171.1, 171.0, 170.9, 154.9, 154.8, 151.8, 151.6, 144.4, 144.3, 137.6, 137.1, 133.1, 132.9, 130.0, 129.9, 129.5, 129.2, 127.9, 127.9, 126.5, 126.1, 122.9, 122.7, 120.7, 120.5.

Prep 11 Synthesis of N-(Toluene-4-sulfonyl)-L-(5,5-dimethyl)thiaprolyl-L-4-(N,N-dimethylcarbamyloxy)phenylalanine Isopropyl Ester The title compound was prepared following the procedure outlined for the preparation of Prep 2 and substitution of appropriate starting materials.

NMR data were as follows: 1H NMR (CDCl3): δ=7.76 (d, 2H), 7.35 (d, 2H), 7.22 (d, 2H), 7.01 (m, 3H), 5.05 (m, 1H), 4.85 (m, 1H), 4.57 (d, 1H), 4.38 (d, 1H), 3.86 (s, 1H), 3.19–3.00 (m, 2H), 3.09 (s, 3H), 3.01 (s, 3H), 2.45 (s, 3H), 1.24 (t, 6H), 1.16 (s, 3H), 1.09 (s, 3H). 13C NMR (CDCl3): δ=170.3, 168.4, 154.9, 150.6, 144.8, 132.9, 132.8, 130.3, 130.0, 128.2, 121.7, 73.4, 69.5, 54.5, 53.2, 50.4, 37.7, 36.5, 36.3, 29.0, 23.8, 21.5, 21.4.

Prep 12 Synthesis of N-(Toluene-4-sulfonyl)-L-(5,5-dimethyl)thiaprolyl-L-4-(N,N-dimethylcarbamyloxy)phenylalanine tert-Butyl Ester The title compound was prepared following the procedure outlined for the preparation of Prep 2 and substitution of appropriate starting materials.

NMR data were as follows: 1H NMR (CDCl3): δ=7.75 (d, 2H), 7.34 (d, 2H), 7.23 (d, 2H), 7.05–6.98 (m, 3H), 4.76 (m, 1H), 4.56 (d, 1H), 4.40 (d, 1H), 3.85 (s, 1H), 3.09–3.00 (m, 8H), 2.44 (s, 3H), 1.43 (s, 3H), 1.16 (s, 3H), 1.09 (s, 3H). 13C NMR (CDCl3): δ=169.8, 168.3, 154.9, 150.6, 144.8, 133.2, 132.9, 130.4, 130.0, 128.2, 121.6, 82.6, 73.4, 54.6, 53.8, 50.4, 37.8, 36.5, 36.3, 29.0, 27.7, 23.8, 21.5.

Prep 13 Synthesis of N-(Toluene-4-sulfonyl)-L-(5,5-dimethyl)thiaprolyl-L-4-(N,N-dimethylcarbamyloxy)phenylalanine The title compound was prepared from the product of Prep 11 using the procedure described in Method 7.

NMR data were as follows: 1H NMR (CDCl3): δ=7.76 (d, 2H), 7.35 (d, 2H), 7.25 (d, 2H), 7.14 (d, 1H), 7.02 (d, 2H), 5.17 (br s, 1H), 4.89 (m, 1H), 4.56 (d, 1H), 4.40 (d, 1H), 3.90 (s, 1H), 3.30–3.00 (m, 8H), 2.43 (s, 3H), 1.09 (s, 6H). 13C NMR (CDCl3): δ=172.7, 169.3, 155.2, 150.6, 144.9, 133.1, 132.7, 130.5, 130.1, 128.1, 121.9, 73.3, 54.5, 53.3, 50.5, 36.9, 36.6, 36.4, 29.0, 23.7, 21.5.

Prep 18 Synthesis of N-(Toluene-4-sulfonyl)sarcosyl-L-4-(N,N-dimethylcarbamyloxy)phenylalanine Isopropyl Ester The title compound was prepared following the procedure outlined for the preparation of Prep 2 and substitution of appropriate starting materials.

NMR data were as follows: 1H NMR (CDCl3): δ=7.66 (d, 2H), 7.34 (d, 2H), 7.18 (d, 2H), 7.07 (d, 2H), 6.98 (d, 1H), 5.03 (m, 1H), 4.81 (m, 1H), 3.69 (d, 1H), 3.49 (d, 1H), 3.08 (m, 2H), 3.04 (s, 3H), 2.99 (s, 3H), 2.63 (s, 3H), 2.43 (s, 3H). 13C NMR (CDCl3): δ=167.4, 154.9, 150.8, 144.4, 132.6, 130.2, 130.1, 127.7, 122.0, 110.9, 69.5, 57.3, 53.9, 53.0, 37.1, 36.6, 21.6, 21.4.

Prep 19 Synthesis of N-(Toluene-4-sulfonyl)sarcosyl-L-4-(N,N-dimethylcarbamyloxy)phenylalanine tert-Butyl Ester The title compound was prepared following the procedure for the preparation of Prep 2 and substitution of appropriate starting materials.

NMR data were as follows: 1H NMR (CDCl3): δ=7.67 (d, 2H), 7.34 (d, 2H), 7.19 (d, 2H), 7.03 (d, 2H), 6.98 (d, 1H), 4.76 (m, 1H), 3.67 (q, 1H), 3.06 (m, 2H), 3.16 (s, 3H), 2.99 (s, 3H), 2.64 (s, 3H), 2.43 (s, 3H), 1.42 (s, 9H). 13C NMR (CDCl3): δ=170.0, 137.2, 154.9, 150.7, 144.3, 133.2, 132.9, 130.3, 130.0, 127.7, 121.9, 82.6, 83.9, 53.3, 37.2, 36.6, 36.4, 27.9, 21.4.

Prep 20 Synthesis of N-(Toluene-4-sulfonyl)sarcosyl-L-4-(N,N-dimethylcarbamyloxy)phenylalanine (Reference Compound 8)

The title compound was prepared from the product of Prep 18 using the procedure described in Method 7.

NMR data were as follows: 1H NMR (CDCl3): δ=7.41 (d, 2H), 7.10 (d, 2H), 6.98 (d, 2H), 6.75 (d, 2H), 4.42 (m, 1H), 3.43 (m, 2H), 3.04 (m, 2H), 2.80 (s, 3H), 2.69 (s, 3H), 2.33 (s, 3H), 2.14 (s, 3H). 13C NMR (CDCl3): δ=174.2, 170.2, 156.9, 151.9, 145.6, 135.5, 135.2, 131.4, 131.1, 128.9, 123.0, 54.6, 54.0, 37.4, 36.8, 36.7, 21.4.

Prep 29 Synthesis of N-(Toluene-4-sulfonyl)-L-(1,1-dioxo-5,5-dimethyl)-thiaprolyl-L-4-(N,N-dimethylcarbamyloxy)phenylalanine tert-Butyl Ester The product of Prep 12 was oxidized by the method of Larsson and Carlson (Acta Chemica Scan. 1994, 48, 517–525), yielding the title compound as a white solid.

NMR data were as follows: 1H NMR (CDCl3): δ=7.73 (d, 2H), 7.36 (d, 2H), 7.21 (d, 2H), 7.06–6.95 (m, 3H), 4.79 (m, 1H), 4.38 (dd, 2H), 4.10 (s, 1H), 3.18–2.95 (m, 8H), 2.43 (s, 3H), 1.45 (s, 9H), 1.33 (s, 3H), 1.08 (s, 3H). 13C NMR (CDCl3): δ=169.8, 166.2, 154.9, 120.7, 145.8, 133.0, 131.9, 130.2, 128.5, 121.9, 82.9, 68.0, 60.9, 59.3, 53.9, 37.5, 36.6, 36.3, 27.7, 21.6, 19.3, 18.5.

Prep 30 Synthesis of N-(1-Methylimidazolyl-4-sulfonyl)-L-prolyl-L-4-(N,N-dimethylcarbamyloxy)phenylalanine The title compound was prepared from the product of Example 106 using the procedure described in Method 11.

NMR data were as follows: 1H NMR (CDCl3): δ=8.07 (d, 1H), 7.75 (s, 1H), 7.71 (s, 1H), 7.25 (d, 2H), 7.01 (d, 2H), 4.71–4.66 (m, 1H), 4.28–4.24 (m, 1H), 3.77 (s, 3H), 3.42–3.05 (m, 3H), 3.09 (s, 3H), 2.96 (s, 3H), 1.84–1.69 (m, 2H), 1.61–1.54 (m, 2H). 13C NMR (CDCl3): δ=174.4, 174.1, 156.9, 151.9, 141.8, 137.7, 135.6, 131.6, 127.6, 122.9, 63.7, 54.7, 50.8, 37.4, 36.8, 36.7, 34.3, 31.6, 25.4.

Prep 31 Synthesis of N-(Toluene-4-sulfonyl)-L-(1,1-dioxo-5,5-dimethyl)-thiaprolyl-L-4-(N,N-dimethylcarbamyloxy)phenylalanine (Reference Compound 4)

The title compound was prepared from the product of Prep 29 using the procedure described in Method 11.

NMR data were as follows: 1H NMR (CDCl3): δ=7.75 (m, 3H), 7.29 (m, 4H), 7.08 (d, 2H), 4.95 (m, 1H), 4.46–4.20 (m, 3H), 3.17 (s, 3H), 3.30–3.10 (m, 2H), 3.02 (s, 3H), 2.43 (s, 3H), 1.15 (s, 3H), 0.88 (s, 3H). 13C NMR (CDCl3): δ=127.2, 167.5, 155.8, 150.3, 145.4, 133.6, 132.6, 130.8, 130.2, 128.3, 121.9, 67.9, 65.8, 60.8, 53.9, 36.8, 36.6, 35.8, 21.6, 18.8, 15.0.

Prep 49 Synthesis of N-(Toluene-4-sulfonyl)-L-(thiamorpholin-3-carbonyl)-L-4-(N,N-dimethylcarbamyloxy)phenylalanine tert-Butyl Ester L-Thiamorpholine-3-carboxylic acid was prepared by the method of Larsson and Carlson (Acta Chemica Scan. 1994, 48, 517–525). N-(Toluene-4-sulfonyl)-L-thiamorpholine-3-carboxylic acid was prepared using the procedure described in Method 1. The title compound was prepared following the procedure for the synthesis of Prep 2 with substitution of appropriate starting materials.

NMR data were as follows: 1H NMR (CDCl3): δ=7.69 (d, 2H), 7.31 (d, 2H), 7.16 (d, 2H), 6.98 (d, 2H), 6.68 (d, 1H), 4.71 (m, 1H), 4.62 (m, 1H), 3.94 (m, 1H), 3.31 (m, 1H), 3.09 (m, 4H), 2.98 (s, 3H), 2.67 (m, 1H), 2.50 (m, 1H), 2.40 (s, 3H), 2.31 (m, 1H), 2.10 (m, 1H), 1.49 (s, 9H). 13C NMR (CDCl3): δ=169.9, 167.4, 154.8, 150.6, 144.2, 136.8, 132.8, 130.4, 130.2, 127.3, 121.8, 82.6, 55.2, 54.0, 43.3, 36.5, 36.3, 27.8, 25.2, 24.6, 21.4.

Prep 50 Synthesis of N-(Toluene-4-sulfonyl) sarcosyl-L-4-(1,1-dioxothiomorpholin-4-ylcarbonyloxy)phenylalanine The title compound was prepared from the product of Prep 121 using the procedure described in Method 11.

NMR data were as follows: 1H NMR (CD3OD): δ=7.67 (d, 2H), 7.40 (d, 2H), 7.27 (d, 2H), 7.09 (d, 2H), 4.61 (m, 1H), 4.12 (m, 2H), 3.99 (m, 2H), 3.60 (m, 2H), 3.23 (m, 8H), 2.58 (s, 3H), 2.42 (s, 3H). 13C NMR (CD3OD): δ=174.2, 170.3, 155.0, 151.6, 145.6, 136.1, 135.2, 131.5, 131.1, 128.9, 123.0, 54.6, 54.0, 52.4, 52.2, 44.4, 44.0, 37.4, 36.8, 21.4.

Prep 51 Synthesis of N-(Toluene-4-sulfonyl)-L-(1,1-dioxothiamorpholin-3-carbonyl)-L-4-(N,N-dimethylcarbamyloxy)phenylalanine tert-Butyl Ester The title compound was prepared from the product of Prep 49 following the procedure described by Larsson and Carlson (Acta Chemica Scan. 1994, 48, 522).

NMR data were as follows: 1H NMR (CDCl3): δ=7.76 (d, 2H), 7.37 (d, 2H), 7.08 (d, 2H), 6.98 (d, 2H), 6.56 (d, 1H), 4.95 (m, 1H), 4.62 (m, 1H), 3.99 (m, 2H), 3.25 (m, 1H), 3.07 (s, 3H), 2.97 (m, 8H), 2.44 (s, 3H), 1.48 (s, 9H). 13C NMR (CDCl3): δ=170.0, 164.8, 154.9, 150.7, 145.4, 135.3, 132.6, 130.7, 130.3, 127.5, 122.3, 82.8, 56.1, 53.6, 49.5, 48.6, 41.6, 36.6, 36.4, 27.9, 21.6.

Prep 60 Synthesis of N-(Toluene-4-sulfonyl)-L-(1,1-dioxothiamorpholin-3-carbonyl)-L-4-(N,N-dimethylcarbamyloxy)phenylalanine (Reference Compound 6)

The title compound was prepared from the product of Prep 51 using the procedure described in Method 11.

NMR data were as follows: 1H NMR (CDCl3): δ=7.79 (d, 2H), 7.43 (d, 2H), 7.20 (d, 2H), 7.00 (d, 2H), 5.21 (m, 1H), 4.65 (m, 1H), 4.12 (m, 1H), 3.75 (m, 1H), 3.29 (m, 3H), 3.08 (s, 3H), 3.00 (m, 1H), 3.00 (m, 1H), 2.97 (s, 3H), 2.80 (m, 3H), 2.44 (s, 3H). 13C NMR (CDCl3): δ=165.1, 159.0, 147.9, 143.1, 137.6, 128.6, 126.1, 122.7, 122.6, 119.8, 114.3, 48.3, 45.8, 41.6, 34.0, 28.0, 27.8, 27.7, 12.5.

While the invention has been described with reference to specific methods and embodiments, it will be appreciated that various modifications and changes may be made without departing from the invention.

It is claimed:

1. A method of treating an inflammatory disorder in a mammalian patient, which disorder involves binding of alpha-9 integrin to an alpha-9 integrin ligand in a mammalian patient, and which disorder is selected from the group consisting of asthma, rheumatoid arthritis, multiple sclerosis, viral meningitis, encephalitis, and ulcerative colitis said method comprising administering to a mammalian subject in need thereof an effective dosage of an alpha-9 integrin antagonist compound which compound is represented by the formula:

wherein:

$R^1$ is selected from the group consisting of alkyl, substituted alkyl, aryl, substituted aryl, cycloalkyl, substituted cycloalkyl, heterocyclic, substituted heterocyclic, heteroaryl and substituted heteroaryl;

$R^2$ is selected from the group consisting of hydrogen, alkyl, cycloalkyl, substituted cycloalkyl, cycloalkenyl, substituted cycloalkenyl, heterocyclic, substituted heterocyclic, substituted alkyl, aryl, substituted aryl, heteroaryl, substituted heteroaryl, and $R^1$ and $R^2$ together with the nitrogen atom bound to $R^2$ and the $SO_2$ group bound to $R^1$ can form a heterocyclic or a substituted heterocyclic group;

$R^3$ is selected from the group consisting of hydrogen, alkyl, substituted alkyl, cycloalkyl, substituted cycloalkyl, aryl, substituted aryl, heteroaryl, substituted heteroaryl, heterocyclic, substituted heterocyclic and, when $R^2$ does not form a heterocyclic group with $R^1$, $R^2$ and $R^3$ together with the nitrogen atom bound to $R^2$ and the carbon atom bound to $R^3$ can form a heterocyclic or a substituted heterocyclic group;

$R^5$ is $-(CH_2)_x-Ar-R^{5'}$ where $R^{5'}$ is selected from the group consisting of $-O-Z-NR^8R^{8'}$ and $-O-Z-R^{12}$ wherein $R^8$ and $R^{8'}$ are independently selected from the group consisting of hydrogen, alkyl, substituted alkyl, cycloalkyl, substituted cycloalkyl, heterocyclic, substituted heterocyclic, and where $R^8$ and $R^{8'}$ are joined to form a heterocyclic or substituted heterocycle, $R^{12}$ is selected from the group consisting of heterocycle and substituted heterocycle, and Z is selected from the group consisting of $-C(O)-$ and $-SO_2-$, Ar is aryl, heteroaryl, substituted aryl or substituted heteroaryl, X is an integer of from 1 to 4;

Q is $-C(X)NR^7-$ wherein $R^7$ is selected from the group consisting of hydrogen and alkyl; and X is selected from the group consisting of oxygen and sulfur; and pharmaceutically acceptable salts thereof, wherein said compound has a $K_i$ or $IC_{50}$ of less than 100 μM, as determined in an assay that measures inhibition of binding between alpha-9 integrin and alpha-9 integrin ligand.

2. The method of claim 1, wherein said inflammatory disorder is characterized by increased neutrophil activity.

3. The method of claim 2, wherein said alpha-9 integrin antagonist compound is selected from a group of compounds which are both alpha-4 integrin and alpha-9 integrin antagonists.

4. A method for treating an inflammatory disorder in a mammalian subject, which disorders are characterized by increased neutrophil activity and involves binding of alpha-9 integrin to an alpha-9 integrin ligand, and which disorder is selected from the group consisting of asthma, rheumatoid arthritis, multiple sclerosis, viral meningitis, encephalitis, and ulcerative colitis wherein the method comprises administering to the mammalian subject in need thereof an alpha-9 integrin antagonist compound selected from the group consisting of:

N-(toluene-4-sulfonyl)-L-prolyl-L-4-(4-methylpiperazin-1-ylcarbonyloxy)phenylalanine, N-(toluene-4-sulfonyl)-L-prolyl-L-4(N,N-dimethylcarbamyloxy)phenylalanine, N-(1-methylpyrazole-4-sulfonyl)-L-prolyl-L-4-(N,N-dimethylcarbamyloxy)phenylalanine, N-(toluene-4-sulfonyl-)-L-(1,1-dioxo-5,5-dimethyl) thiaprolyl-L-4(N,N-dimethylcarbamyloxy) phenylalanine, N-(toluene-4-sulfonyl)-N-methyl-L-alaninyl-L-4-(N,N-dimethylcarbamyloxy)phenylalanine, N-(toluene-4-sulfonyl)-L-[(1,1-dioxo)thiamorpholin-3-carbonyl]-L-4-(N,N-dimethylcarbamyloxy) phenylalanine, N-(N-p-toluenesulfonyl)prolyl-4-(piperazinoyloxy) phenylalanine, N-(N-p-toluenesulfonyl)sarcosyl-4-(N,N-dimethylcarbamyloxy)phenylalanine, N-(toluene-4-sulfonyl)-L-(5,5-dimethyl)thiaprolyl-L-4-[3-(N,N-dimethyl)propoxy]-phenylalanine, and pharmaceutically acceptable salts thereof.

5. The method of claim 1, wherein the alpha-9 integrin ligand is vascular cell adhesion molecule-1 (VCAM-1).

6. The method of claim 1, wherein the alpha-9 integrin antagonist compound inhibits binding between alpha-9 integrin and an alpha-9 integrin ligand, wherein the ligand is selected from the group consisting of osteopontin, tenascin, VCAM-1, and combinations thereof.

7. A method for inhibiting binding of alpha-9 integrin to an alpha-9 integrin ligand in a mammalian subject, the method comprising administering to a mammalian subject in need thereof a an alpha-9 integrin antagonist compound, which compound is represented by the formula:

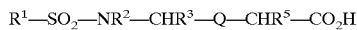

wherein:

$R^1$ is selected from the group consisting of alkyl, substituted alkyl, aryl, substituted aryl, cycloalkyl, substituted cycloalkyl, heterocyclic, substituted heterocyclic, heteroaryl and substituted heteroaryl;

$R^2$ is selected from the group consisting of hydrogen, alkyl, cycloalkyl, substituted cycloalkyl, cycloalkenyl, substituted cycloalkenyl, heterocyclic, substituted heterocyclic, substituted alkyl, aryl, substituted aryl, heteroaryl, substituted heteroaryl, and $R^1$ and $R^2$ together with the nitrogen atom bound to $R^2$ and the $SO_2$ group bound to $R^1$ can form a heterocyclic or a substituted heterocyclic group;

$R^3$ is selected from the group consisting of hydrogen, alkyl, substituted alkyl, cycloalkyl, substituted cycloalkyl, aryl, substituted aryl, heteroaryl, substituted heteroaryl, heterocyclic, substituted heterocyclic and, when $R^2$ does not form a heterocyclic group with $R^1$, $R^2$ and $R^3$ together with the nitrogen atom bound to $R^2$ and the carbon atom bound to $R^3$ can form a heterocyclic or a substituted heterocyclic group;

$R^5$ is $-(CH_2)_x-Ar-R^{5'}$ where $R^{5'}$ is selected from the group consisting of $-O-Z-NR^8R^{8'}$ and $-O-Z-R^{12}$ wherein $R^8$ and $R^{8'}$ are independently selected from the group consisting of hydrogen, alkyl, substituted alkyl, cycloalkyl, substituted cycloalkyl, heterocyclic, substituted heterocyclic, and where $R^8$ and $R^{8'}$ are joined to form a hetero cyclic or substituted heterocycle, $R^{12}$ is selected from the group consisting of heterocycle and substituted heterocycle, and Z is selected from the group consisting of $-C(O)-$ and $-SO_2-$, Ar is aryl, heteroaryl, substituted aryl or substituted heteroaryl, X is an integer of from 1 to 4;

Q is $-C(X)NR^7-$ wherein $R^7$ selected from the group consisting of hydrogen and alkyl; and X is selected from the group consisting of oxygen and sulfur; and pharmaceutically acceptable salts thereof.

8. The method of claim 7, wherein said alpha-9 integrin antagonist compound is selected from a group of compounds which are both alpha-4 integrin and alpha-9 integrin antagonists.

* * * * *